United States Patent
van Zijl et al.

(10) Patent No.: US 12,405,333 B2
(45) Date of Patent: Sep. 2, 2025

(54) MAGNETIC RESONANCE IMAGING OF GLYCOGEN AND OTHER POLYSACCHARIDES BY MAGNETIC COUPLING WITH WATER

(71) Applicants: The Johns Hopkins University, Baltimore, MD (US); Kennedy Krieger Institute, Inc., Baltimore, MD (US)

(72) Inventors: Peter van Zijl, Baltimore, MD (US); Yang Zhou, Baltimore, MD (US); Nirbhay N. Yadav, Baltimore, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 187 days.

(21) Appl. No.: 18/037,726

(22) PCT Filed: Nov. 19, 2021

(86) PCT No.: PCT/US2021/060214
§ 371 (c)(1),
(2) Date: May 18, 2023

(87) PCT Pub. No.: WO2022/115339
PCT Pub. Date: Jun. 2, 2022

(65) Prior Publication Data
US 2023/0408611 A1 Dec. 21, 2023

Related U.S. Application Data

(60) Provisional application No. 63/117,774, filed on Nov. 24, 2020.

(51) Int. Cl.
*G01V 3/00* (2006.01)
*G01R 33/48* (2006.01)

(52) U.S. Cl.
CPC .................. *G01R 33/4828* (2013.01)

(58) Field of Classification Search
CPC .............. G01R 33/287; G01R 33/4835; G01R 33/5608; A61B 2090/374
(Continued)

(56) References Cited

U.S. PATENT DOCUMENTS

| | | | |
|---|---|---|---|
| 2003/0017110 A1 | 1/2003 | Pines et al. | |
| 2008/0197840 A1* | 8/2008 | Van Zijl | G01R 33/485 324/307 |

(Continued)

FOREIGN PATENT DOCUMENTS

| | | | | |
|---|---|---|---|---|
| CN | 1283202 A | * | 2/2001 | ......... C07K 14/4716 |
| CN | 102645491 A | * | 8/2012 | |

(Continued)

OTHER PUBLICATIONS

Zhou et al. "Magnetic resonance imaging of glycogen using its magnetic coupling with water", In: Proceedings of the National Academy of Sciences, Feb. 11, 2020, vol. 117, No. 6, pp. 3144-3149.

(Continued)

*Primary Examiner* — Walter L Lindsay, Jr.
*Assistant Examiner* — Frederick Wenderoth
(74) *Attorney, Agent, or Firm* — Venable LLP; Henry J. Daley

(57) ABSTRACT

Some embodiments provide a method for magnetic resonance imaging of polysaccharide molecules, that includes providing a magnetic field that is sufficiently homogeneous over an imaging volume, generating a spatial encoding in the magnetic field, and acquiring one or more water proton signal intensity measurements at each of multiple voxels within the imaging volume. The signal intensity measurements are acquired at one or more irradiation frequencies at (Continued)

lower parts-per-million (ppm) than a baseline frequency associated with free water protons. The method includes generating, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume, and generating, using a calibration of the water proton signal intensity measurements for the rNOE exchange process, a concentration map of the polysaccharide molecules in the imaging volume.

30 Claims, 29 Drawing Sheets

(58) Field of Classification Search
USPC .......................................................... 324/309
See application file for complete search history.

(56) References Cited

U.S. PATENT DOCUMENTS

| 2009/0045811 | A1 | 2/2009 | Sasisekharan et al. |
| 2012/0271159 | A1* | 10/2012 | Song .................. G01R 33/5601 600/420 |

FOREIGN PATENT DOCUMENTS

| WO | WO-2007141767 A2 * | 12/2007 | ......... A61K 49/0002 |
| WO | 2019/143801 A1 | 7/2019 | |

OTHER PUBLICATIONS

Van Heeswijk et al. "Quantification of brain glycogen concentration and turnover through localized 13C NMR of both the C1 and C6 resonances", NMR in Biomedicine., (2010), vol. 23, pp. 270-276.
Brown et al., "Astrocyte glycogen and brain energy metabolism", Glia., (2007), vol. 55, pp. 1263-1271.
Gruetter et al., "Validation of 13C NMR measurements of liver glycogen in vivo", Magnetic resonance in medicine, (1994), vol. 31, pp. 583-588.
Konig et al., "Quantifying the contribution of the liver to glucose homeostasis: a detailed kinetic model of human hepatic glucose metabolism", PLoS Comp Bio., (2012), vol. 8, Issue 6, (17 pages).
Hennig et al., "Contribution of glycogen to aerobic myocardial glucose utilization", Circulation, (1996), vol. 93, (21 pages).
Price et al., "13C-NMR measurements of muscle glycogen during low-intensity exercise", J Appl Physiology., (1991), vol. 70, pp. 1836-1844.
Ortenblad et al., "Muscle glycogen stores and fatigue", J Physiology., (2013), vol. 591, No. 18, pp. 4405-4413.
Rousset et al., "Presence of glycogen and growth-related variations in 58 cultured human tumor cell lines of various tissue origins", Cancer Res., (Mar. 1981), vol. 41, pp. 1165-1170.
Favaro et al., "Glucose utilization via glycogen phosphorylase sustains proliferation and prevents premature senescence in cancer cells", Cell Metabolism., (Dec. 5, 2012), vol. 16, pp. 751-764.
Magnusson et al., "Increased rate of gluconeogenesis in type II diabetes mellitus: A 13C nuclear magnetic resonance study", J Clin Invest., (1992), vol. 90, pp. 1323-1327.
Krssak et al., "Alterations in postprandial hepatic glycogen metabolism in type 2 diabetes", Diabetes., (Dec. 2004), vol. 53, pp. 3048-3056.
Adeva-Andany et al., "Glycogen metabolism in humans", BBA Clinical., (2016), vol. 5, pp. 85-100.
Krahenbuhl et al., "Reduced hepatic glycogen stores in patients with liver cirrhosis", Liver Int., (2003), vol. 23, pp. 101-109.

Nieman et al., "Ultrasonic assessment of exercise-induced change in skeletal muscle glycogen content", BMC Sports Science, Medicine, and Rehabilitation, (2015), vol. 7, No. 9, (7 pages).
Witney et al., "A novel radiotracer to image glycogen metabolism in tumors by positron emission tomography", Cancer Res., (2014), vol. 74, No. 5, pp. 1319-1328.
Sillerud et al., "Structure and metabolism of mammalian liver glycogen monitored by carbon-13 nuclear magnetic resonance", Biochemistry., (1983), vol. 22, pp. 1087-1094.
Zang et al., "1H NMR visibility of mammalian glycogen in solution", PNAS., (Mar. 1990), vol. 87, pp. 1678-1680.
Heinicke et al., "Reproducibility and Absolute Quantification of Muscle Glycogen in Patients with Glycogen Storage Disease by 13C NMR Spectroscopy at 7 Tesla", PLoS One, (Oct. 2014), vol. 9, Issue 10, (6 pages).
Roser et al., "Absolute quantification of the hepatic glycogen content in a patient with glycogen storage disease by 13C magnetic resonance spectroscopy", Magnetic Resonance Imaging., (1996), vol. 14, No. 10, pp. 1217-1220.
Ouwerkerk et al., "Liver metabolite concentrations measured with 1H MR spectroscopy", Radiology., (Nov. 2012), vol. 265, No. 2, pp. 565-575.
Van Zijl et al., "MRI detection of glycogen in vivo by using chemical exchange saturation transfer imaging (glycoCEST)", PNAS., (Mar. 13, 2007), vol. 104, No. 11, pp. 4359-4364.
Miller et al., "Noninvasive Measurements of Glycogen in Perfused Mouse Livers Using Chemical Exchange Saturation Transfer NMR and Comparison to 13C NMR Spectroscopy", Analytical Chemistry., (2015), vol. 87, pp. 5824-5830.
Simegn et al., "Real-time simultaneous shim and motion measurement and correction in glycoCEST MRI using double volumetric navigators (DvNavs)", Mag Resonance in Medicine., (2019), vol. 81, pp. 2600-2613.
Van Zijl et al., "Chemical exchange saturation transfer (CEST): what is in a name and what isn't?", Magnetic resonance in medicine., (2011), vol. 65, pp. 927-948.
Deng et al., "Chemical exchange saturation transfer (CEST) MR techniqu,e for liver imaging at 3.0 Tesla: an evaluation of different offset No. and an after-meal and over-night fast comparison", Mol Imaging and Biology., (2016), vol. 18, pp. 274-282.
Chen et al., "NMR studies of proton NOEs in glycogen", Biochemistry, (1993), vol. 32, pp. 11483-11487.
Ling et al., "Assessment of glycosaminoglycan concentration in vivo by chemical exchange-dependent saturation transfer (gagCEST)", PNAS., (Feb. 19, 2008), vol. 105, No. 7, pp. 2266-2270.
Yadav et al., "Detection of dynamic substrate binding using MRI", Sci Reports., (2017), vol. 7, (7 pages).
Zang et al., "Assignment of the 1H chemical shifts of glycogen", Carbohydrate Research., (1991), vol. 220, pp. 1-9.
Desmond et al., "Mapping of amide, amine, and aliphatic peaks in the CEST spectra of murine xenografts at 7 T", Mag Resonance in Medicine., (2014), vol. 71, pp. 1841-1853.
Giffin et al., "Hepatic lobular patterns of phosphoenolpyruvate carboxykinase, glycogen synthase, and glycogen phosphorylase in fasted and fed rats", J Histochemistry & Cytochemistry., (1993), vol. 41, No. 12, pp. 1849-1862.
Jensen et al., "Fasting of mice: a review", Lab Animals., (2013), vol. 47, No. 4, pp. 225-240.
Sullivan et al., "Changes in glycogen structure over feeding cycle sheds new light on blood-glucose control", Biomacromolecules., (2014), vol. 15, pp. 660-665.
Chen et al., "Protein aggregation linked to Alzheimer's disease revealed by saturation transfer MRI", NeuroImage., (2019), vol. 188, pp. 380-390.
Chen et al., "Creatine and phosphocreatine mapping of mouse skeletal muscle by a polynomial and Lorentzian line-shape fitting CEST method", Mag Resonance in Medicine., (2019), vol. 81, pp. 69-78.
Zang et al., "Carbon-13 NMR relaxation times of hepatic glycogen in vitro and in vivo", Biochemistry., (1990), vol. 29, pp. 6815-6820.

(56) References Cited

OTHER PUBLICATIONS

Shokri-Afra et al., "Improvement of the classical assay method for liver glycogen fractions: ASG is the main and metabolic active fraction", Eur Rev for Medical and Pharmacological Sciences., (2016), vol. 20, pp. 4328-4336.
Strubelt et al., "The influence of fasting on the susceptibility of mice to hepatotoxic injury", Toxicology and Applied Pharmacology., (1981), vol. 60, pp. 66-77.
Kim et al., Water saturation shift referencing (WASSR) for chemical exchange saturation transfer (CEST) experiments, Mag resonance in medicine., (2009), vol. 61, pp. 1441-1450.
Zhou et al., "Magnetic resonance imaging of glycogen using its magnetic coupling with water", PNAS, (Feb. 11, 2020), vol. 117, No. 6, pp. 3144-3149.
Ishihara et al., "A precise and fast temperature mapping using water proton chemical shift", Magnetic Resonance in Medicine., (1995), vol. 34, pp. 814-823.
Allard et al., "The complete homogeneous master equation for a heteronuclear two-spin system in the basis of cartesian product operators", J Mag Resonance., (1998), vol. 134, pp. 7-16,.
Bloembergen et al., "Relaxation effects in nuclear magnetic resonance absorption", Physical Review, (Apr. 1, 1948), vol. 73, No. 7, (37 pages).
Tylianakis et al., "NMR study of the rotational dynamics of linear homopolysaccharides in dilute solutions as a function of linkage position and stereochemistry", Carbohydrate Research., (1999), vol. 315, pp. 16-34.
Simpson et al., "Diffusion and nuclear spin relaxation in water", Physical Review, (Sep. 1, 1958), vol. 111, No. 5, pp. 2101-1202.
Sagiyama et al., "In vivo monitoring of liver glycogen by chemical exchange saturation transfer imaging (GlycoCEST) in live mice", Proceedings of the International Society for Magnetic Resonance in Medicine, (2014), vol. 22, p. 0762.

\* cited by examiner

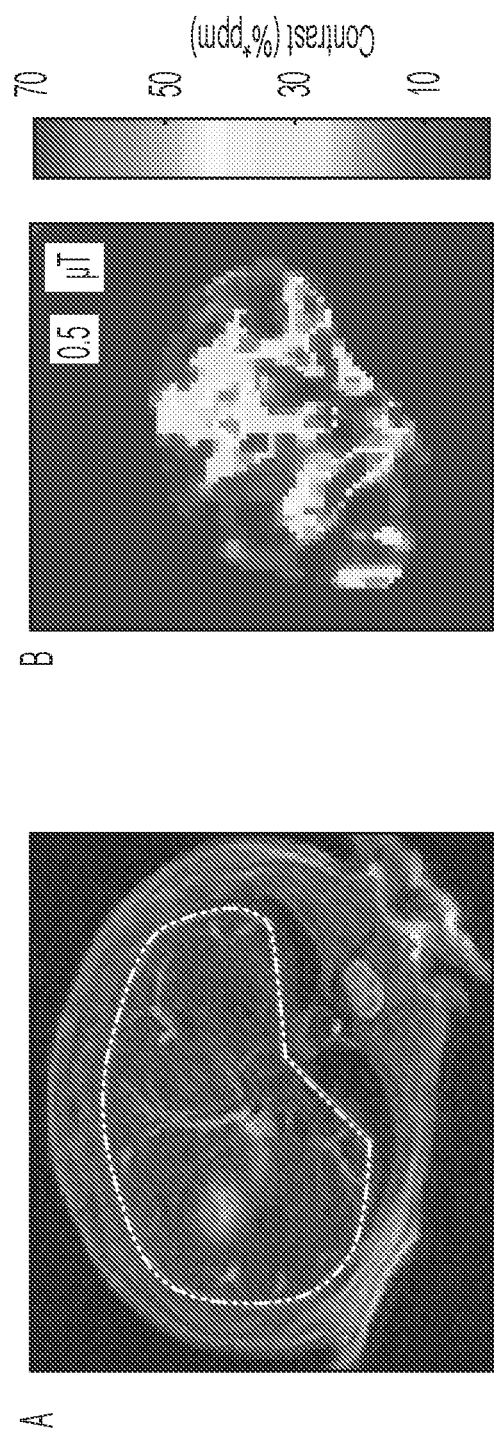
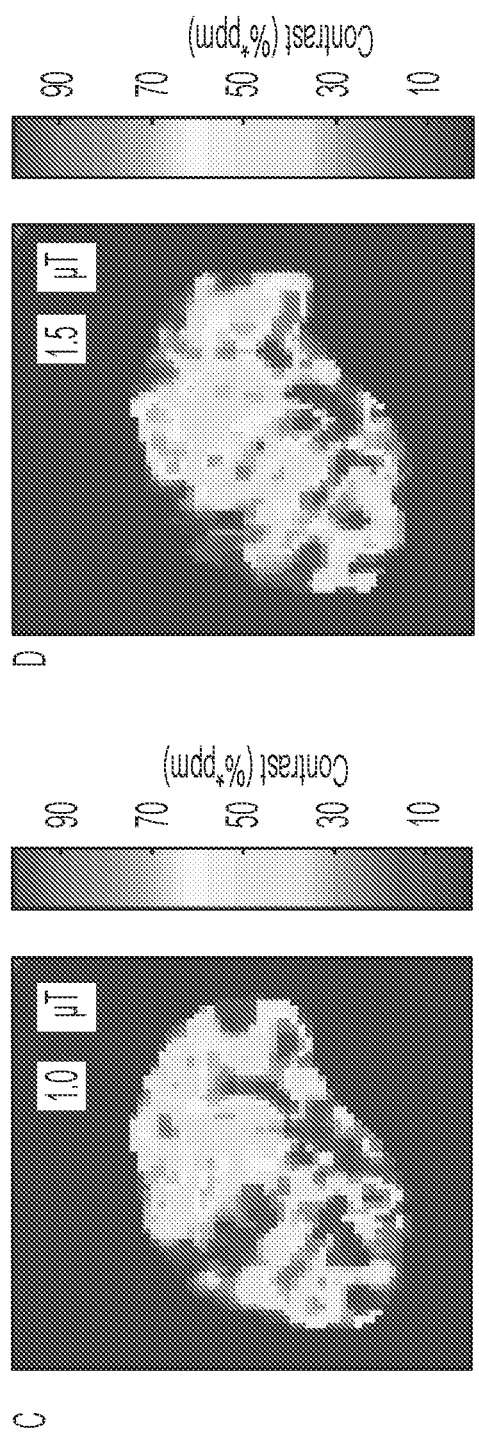
FIG. 9A-9D

MAGNETIC RESONANCE IMAGING OF GLYCOGEN AND OTHER POLYSACCHARIDES BY MAGNETIC COUPLING WITH WATER

This application is a U.S. National Stage of PCT/US2021/60214, filed Nov. 19, 2021, which claims priority to U.S. Provisional Application No. 63/117,774, filed Nov. 24, 2020, which is incorporated herein by reference in its entirety.

This invention was made with government support under grant EB015032 awarded by the National Institutes of Health. The government has certain rights in the invention.

BACKGROUND

1. Technical Field

Embodiments relate to systems and methods for detecting and imaging of glycogen and other polysaccharides using magnetic coupling with water, and specifically using Nuclear Overhauser enhancement (NOE) techniques.

2. Discussion of Related Art

Glycogen is the primary form of glucose storage in mammals, and plays a vital role in cellular energy homeostasis. Mapping glycogen in vivo is useful in the diagnosis and assessment of diseases where glucose metabolism is altered, such as diabetes, cancer, and liver, and muscle diseases. Currently, imaging glycogen in the clinic is not done due to the lack of a practical approach.

Glycogen, a branched polymeric form of glucose, plays a central role in maintaining glucose (short-term energy) homeostasis in different tissues. For instance, brain glycogen (with a concentration of ~5.1 mM (1)) is almost exclusively localized in astrocytes (2) and acts as an energy reserve for neuronal activity. Liver glycogen (100-800 mM (3)) maintains appropriate levels of blood glucose (4), while glycogen in heart muscle is a crucial contributor to myocardial energy production (5). Skeletal muscle glycogen (40-100 mM (6)) storage is closely correlated to fatigue resistance during prolonged or high-intensity exercise (7). Considering its role in cellular energy homeostasis and its wide abundance in vivo, changes in glycogen concentration are often an endogenous marker for a variety of diseases such as, for instance, cancers (8, 9), diabetes (10, 11), glycogen storage diseases (12) and liver diseases (13). A method allowing non-invasive in vivo measurement of glycogen levels would thus be of importance for the assessment of many diseases and disorders.

Several techniques are currently available for quantifying glycogen non-invasively, including ultrasound (14), $^{18}$F-N-(methyl-(2-fluoroethyl)-$^{1}$H-[1,2,3]triazole-4-yl)glucosamine Positron Emission Tomography ($^{18}$F-NFTG-PET) (15), $^{13}$C and $^{1}$H magnetic resonance spectroscopy (MRS) (1, 3, 6, 16-18). The specificity of the MRS methods is superior to ultrasound. While $^{1}$H MRS has been shown to detect the total glycogen pool when dissolved in $D_2O$ in vitro (17), it may underestimate the amount of hepatic glycogen in vivo (19, 20). In vivo $^{13}$C MRS, one of the most popular methods in the past several decades, have been performed at natural abundance (1, 3, 18) (1.1% of all carbons) as well as with infusion of substrate (1), but its impact in the clinic has been limited due to its much lower detection sensitivity compared to $^{1}$H MR and its requirement for specialized equipment that often is unavailable on clinical MRI scanners. $^{18}$F-NFTG-PET study of exogenous isotope-labeled agents detects only the synthesis of labelled glycogen instead of the total glycogen pool.

The glycoCEST (chemical exchange saturation transfer imaging of glycogen) MRI method (21-23) was proposed more than a decade ago as a promising method that does not require specialized hardware or exogenous contrast agents, and provides maps with relatively high spatial resolution. The glycoCEST method detects glycogen indirectly through the exchange interaction between the glycogen hydroxyl protons and water protons, a principle that has been widely utilized to image several other metabolite molecules (24). However, the fast exchange properties of glycogen hydroxyl protons in vivo and the presence of magnetic resonance signals from several other molecular sources at the hydroxyl proton frequencies hinder the quantification of the glycoCEST signal. Consequently, the glycoCEST MRI method has only had limited success for in vivo studies (25, 26).

U.S. Pat. No. 7,683,617 describes earlier work in glycoCEST MRI, and is incorporated by reference herein in its entirety.

SUMMARY

A system for magnetic resonance imaging of polysaccharide molecules. The system includes a primary magnet configured to provide a magnetic field that is sufficiently homogeneous over an imaging volume, a magnetic gradient coil configured to generate a spatial encoding in the magnetic field, and a radiofrequency coil configured to acquire one or more water proton signal intensity measurements at each of multiple voxels within the imaging volume. The signal intensity measurements are acquired in each voxel at a one or more irradiation frequencies, the irradiation frequencies being at lower parts-per-million (ppm) than a baseline frequency associated with free water protons. The system also includes a data processor configured to generate, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume. The data processor is also configured to generate, using a calibration of the water proton signal intensity measurements for the rNOE exchange process, a concentration map of the polysaccharide molecules in the imaging volume.

A method for magnetic resonance imaging of polysaccharide molecules. The method includes providing a magnetic field that is sufficiently homogeneous over an imaging volume, generating a spatial encoding in the magnetic field, and acquiring one or more water proton signal intensity measurements at each of multiple voxels within the imaging volume. The signal intensity measurements are acquired in each voxel at a one or more irradiation frequencies, the irradiation frequencies being at lower parts-per-million (ppm) than a baseline frequency associated with free water protons. The method also includes generating, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume. The method also includes generating, using a calibration of the water proton signal intensity measurements for the rNOE exchange process, a concentration map of the polysaccharide molecules in the imaging volume.

A non-transitory machine-readable medium that includes computer-executable instructions for magnetic resonance imaging of polysaccharide molecules. The instructions, when executed by a computer, cause the computer to configure a primary magnet to provide a magnetic field that is sufficiently homogeneous over an imaging volume, configure a magnetic gradient coil to generate a spatial encoding in the magnetic field, and configure a radiofrequency coil to acquire one or more water proton signal intensity measurements at each of multiple voxels within the imaging volume. The signal intensity measurements are acquired in each voxel at a one or more irradiation frequencies, the irradiation frequencies being at lower parts-per-million (ppm) than a baseline frequency associated with free water protons. The instructions when executed further cause the computer to generate, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume, and generate, using a calibration of the water proton signal intensity measurements for said rNOE exchange process, a concentration map of the polysaccharide molecules in the imaging volume.

BRIEF DESCRIPTION OF THE DRAWINGS

Further objectives and advantages will become apparent from a consideration of the description, drawings, and examples.

FIGS. 9A-9D show anatomical and glycoNOE maps of a fed mouse liver at different $B_1$ strengths at 11.7 T.

DETAILED DESCRIPTION

Figure 1A:
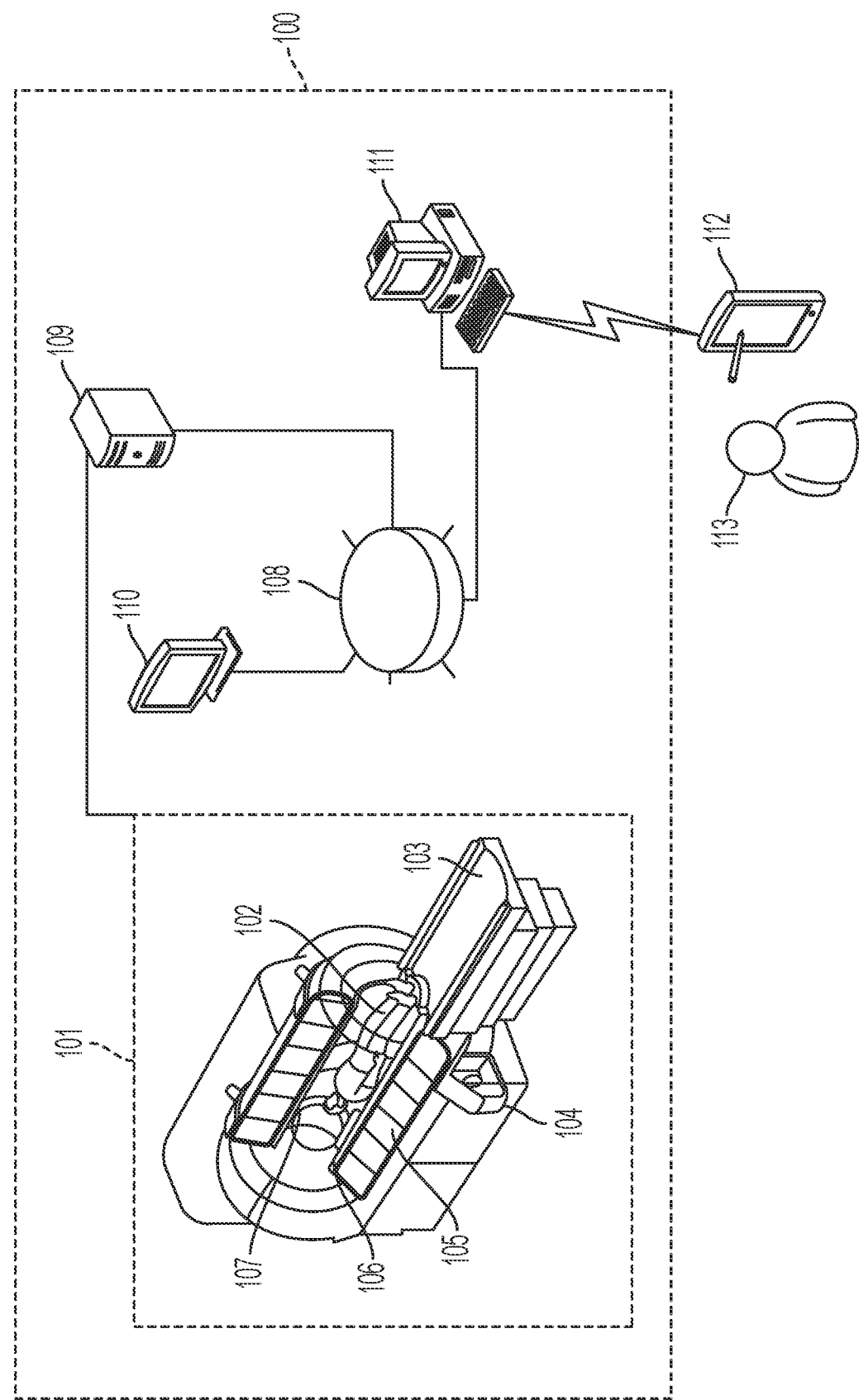
FIG. 1A is a schematic illustration of a system for magnetic resonance imaging of polysaccharide molecules according to some embodiments.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The below-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All references cited anywhere in this specification, including the Background and Detailed Description sections, are incorporated by reference as if each had been individually incorporated.

Some embodiments provide a non-invasive MRI (magnetic resonance imaging) method for directly imaging polysaccharide molecules with enhanced detection sensitivity and high specificity. Examples of polysaccharide molecules that can be directly imaged by some embodiments include glycogen molecules and other carbohydrates with two or more sugar molecules bonded together (carbohydrate dimers and polymers). Additional examples include chemically modified polysaccharide molecules, labelled polysaccharide molecules, polysaccharides connected to binding substrates, endogenous polysaccharides, and exogenous polysaccharides.

Some embodiments of the method provide in vivo mapping of mouse liver glycogen, showing a heterogenous distribution of glycogen and regions of metabolism, enabling studies of glycogen metabolism in vivo at high temporal and spatial resolution. Other embodiments of the method provide in vitro methods.

Further objectives and advantages will become apparent from a consideration of the description, drawings, and examples.

Some embodiments perform direct imaging of glycogen based on the nuclear Overhauser enhancement (NOE) phenomenon (also called nuclear Overhauser effect, when multiple enhancements are measured together) (27). NOE, a fundamental magnetization transfer mechanism, can be detected using saturation transfer (ST) experiments, (24, 28), which are illustrated in FIGS. 1A-1G, described in more detail below. In these experiments, the relative saturation of water signal is measured as a function of saturation frequency, generating a so-called Z-spectrum (FIG. 1F). Like a ¹H MR spectrum (FIGS. 1D and 1E), the Z-spectrum (FIG. 1F) displays signals from different molecular or chemical origin, but with enhanced sensitivity and from protons undergoing saturation transfer via either chemical exchange (FIG. 1G), relayed or direct NOEs (FIGS. 1B and 1C, respectively), or transferred magnetization due to transient molecular binding (29). Based on this rationale, NOEs between water protons and glycogen aliphatic protons (27) are detectable in some embodiments at one or more chemical shift positions in the Z-spectrum.

Figures 1B, 1C, 1D, 1E, 1F, 1G:
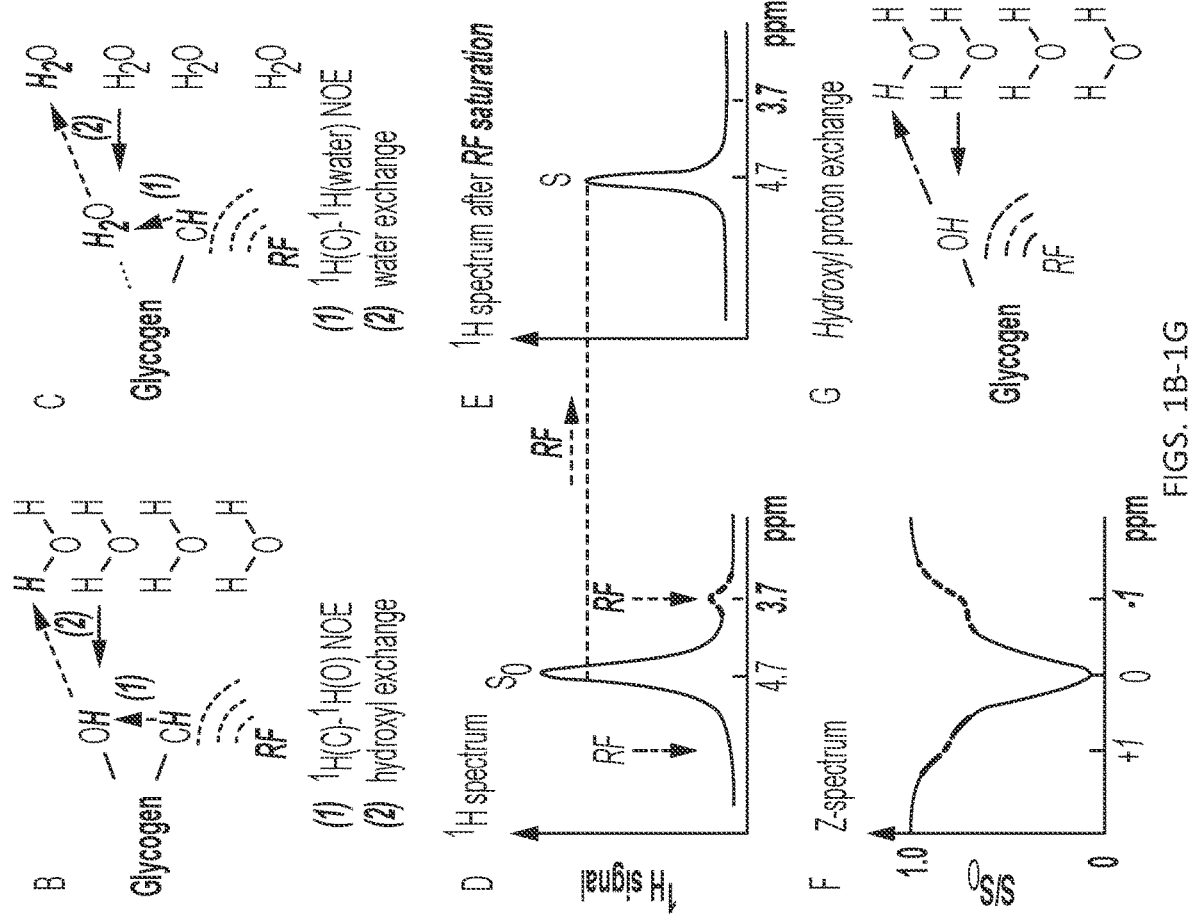
FIGS. 1B-1G illustrate the basics of the glycoNOE saturation transfer experiment acquired with the system of FIG. 1A, according to some embodiments.

FIG. 1A shows a system 100 for magnetic resonance imaging of polysaccharide molecules according to some embodiments. The system 100 includes an MRI system 101. The MRI system 101 can accommodate a subject 102 under observation on scanner bed 103, for example. The MRI system 101 can include, but is not limited to, a primary magnet system 105 providing a substantially uniform main magnetic field $B_0$ for a sample (subject or object) 102 under observation on scanner bed 103, a magnetic gradient coil system 106 providing a perturbation of the main magnetic field B0 to encode spatial information of the constituent molecules of subject 102 under observation, and a radiofrequency (RF) coil system 107 to transmit electromagnetic waves and to receive magnetic resonance signals from subject 102. The RF coil system 107 may include separate radiofrequency transmit and receive coils, each having a plurality of coils. For instance, receivers can have multiple MRI detectors, such as those provided in an 'MRI phased-array.' Some embodiments of the invention include 16, 32, 60, or 120 MRI detectors, though these numbers are provided as examples, and the embodiments of the invention are not limited to these examples. Each MRI detector has a spatial sensitivity map.

The system 100 also has a processor 109 configured to communicate with the MRI system 101. The processor 109 can be partially or totally incorporated within a structure 104 that houses the NMR system 101 and/or partially or totally incorporated in a computer, a server, or a workstation that is structurally separate from and in communication with the NMR system 101.

The system 100 can include a data storage unit 108 that can be, for example, a hard disk drive, a network area storage (NAS) device, a redundant array of independent disks (RAID), a flash drive, an optical disk, a magnetic tape, a magneto-optical disk, or that provided by local or remote computer 'cloud' networking, etc. However, the data storage unit 108 is not limited to these particular examples. It can include other existing or future developed data storage devices without departing from the scope of the current invention.

The processor 109 can be configured to communicate with the data storage unit 108. The processor 109 can also be in communication with a display system 110 and/or a console station 111. In some embodiments, results can be displayed by the display system 110 or the console station 111. In some embodiments, an operator 113 may use an input/output device 112 to interact, control, and/or receive results from system 100.

The MRI system 101 is configured to apply a plurality of spatially localized MRI sequences, wherein each sequence is adjusted to be sensitive to an MRI parameter whose measurement requires the acquisition of a plurality of spatially localized MR signals. The MRI system 101 is configured to adjust at least one of the applied plurality of spatially localized MRI sequences so as to substantially fully sample an image k-space of the sample, and adjust the remainder of the applied plurality of spatially localized MRI sequences to under-sample the image k-space of the sample. The MRI system 101 is configured to acquire a plurality of image k-space MRI signal data sets, each responsive to the application of each of the plurality of spatially localized MRI sequences. The processor 109 is configured to estimate a sensitivity map of each of the plurality of MRI detectors using a strategy to suppress unfolding artefacts, wherein the strategy is based on data acquired from the substantially fully-sampled spatially localized MRI sequence. The processor 109 is configured to apply the estimated sensitivity maps to at least one of the image k-space MRI signal data sets to reconstruct a spatial image of MRI signals that are sensitive to the MRI parameter within a Support Region of the spatial image in which the sample resides.

According to some embodiments of the invention, the MRI system 101 and the processor 109 are associated by one of an Ethernet connection, a Wi-Fi connection, or by integration of the processor 109 into the MRI system 101.

According to some embodiments, the processor 109 is configured to reconstruct an image whose intensity is directly proportional to a spatial distribution of the MRI parameter within the sample 102, and the display system 110 or the console station 111 is configured to display the reconstructed image.

FIGS. 1B-1G illustrate the basics of the glycoNOE saturation transfer experiment performed with the MR system 101 in FIG. 1A. FIGS. 1B and 1C show two possible NOE-based saturation transfer pathways from glycogen aliphatic protons to water. In FIG. 1B, saturation on glycogen aliphatic protons by a radio frequency (RF) pulse is transferred to a neighboring hydroxyl proton, and subsequently to water via proton chemical exchange between glycogen hydroxyl protons and water (relayed NOE). In FIG. 1C, saturation on aliphatic protons is transferred directly to a nearby bound water (direct NOE), and then to the free water pool via water molecular exchange. FIGS. 1D and 1E illustrate a schematic ¹H MR spectrum for glycogen in $H_2O$, before (FIG. 1D) and after (FIG. 1E) the RF saturation of the aliphatic protons. $S_0$ and S represent water intensities in the two spectra. In FIG. 1F, the corresponding Z-spectrum is illustrated, showing $S/S_0$ as a function of RF irradiation frequency. The signal shown at around −1 ppm in the Z-spectrum is from glycogen aliphatic protons undergoing the possible NOE based saturation transfer mechanisms (FIGS. 1B and 1C), while the signal at around +1 ppm is from hydroxyl protons undergoing chemical exchange with water (FIG. 1G). Because of multiple repeated saturation transfer events in a single MR sequence, the glycogen signal in the Z-spectrum is enhanced compared to that in the ¹H MR spectrum. Note that the Z-spectrum, for convenience, is referenced to the water frequency assigned to be 0 ppm, while it is 4.7 ppm in the MR spectrum.

In some in vivo embodiments, NOE occurs between the aliphatic protons of a polysaccharide (e.g., the solute) and free water (e.g., the solvent). In some embodiments, the solute is dextran.

The following describes some particular embodiments of the current invention in more detail; however, the general concepts of the current invention are not to be limited to these particular examples.

As described below, glycogen NOE signals were characterized in vitro by varying glycogen concentration, pH and temperature. In addition, in vivo NOE signals were also used to image glycogen in mouse liver. Both in vitro and in vivo cases showed a strong signal around −1 ppm relative to the water resonance in the aliphatic region of the Z-spectrum. To validate that the in vivo signal source was from glycogen, the signal changes in the liver of fed mice were examined before and after 24 hours fasting, as well as the effect of intraperitoneal injection of glucagon, which is known to rapidly deplete hepatic glycogen.

Experimental Results

Figures 2A, 2B, 2C, 2D, 2E:
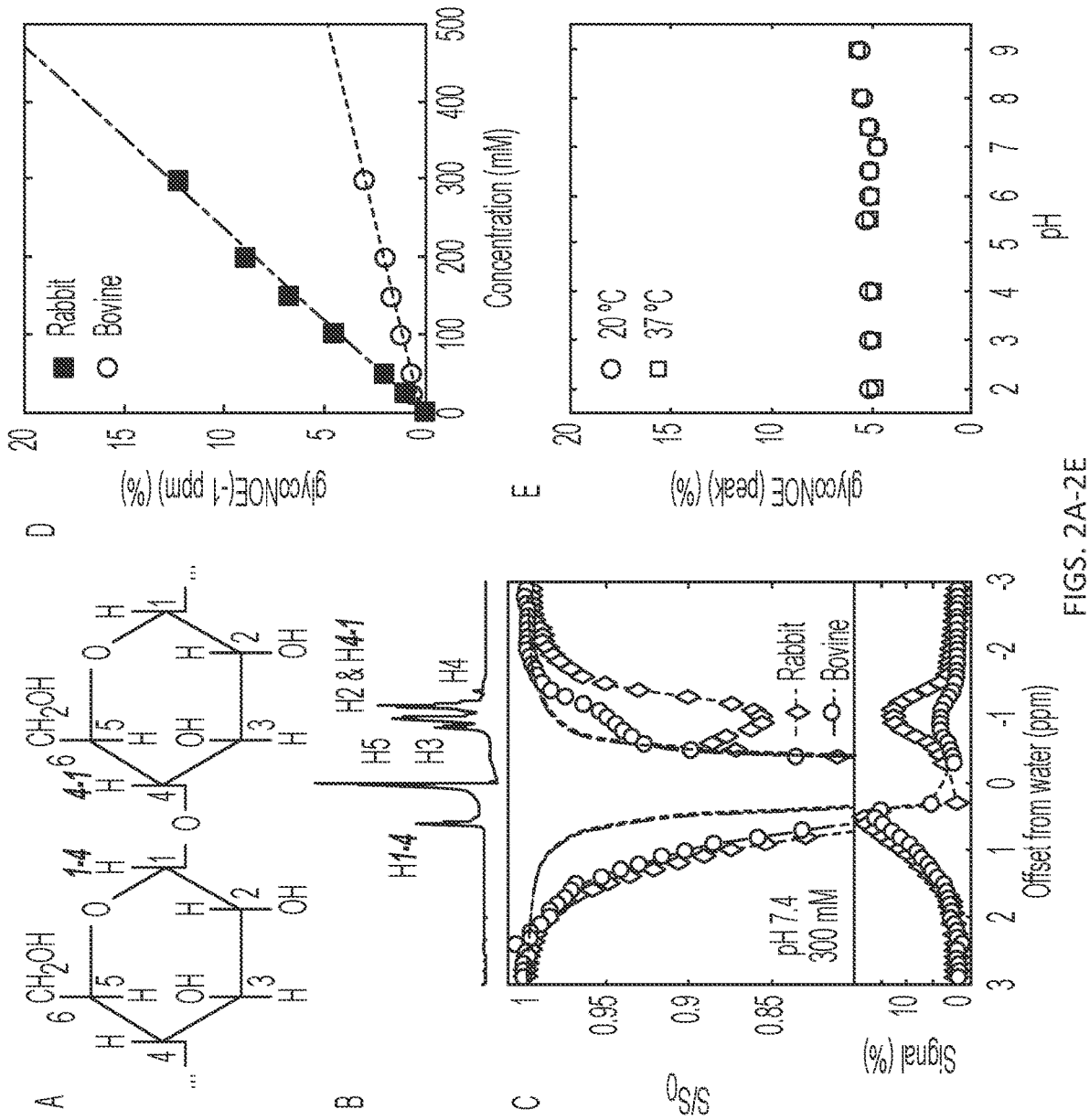
FIGS. 2A-2E show an example of a glycoNOE signal in vitro for liver glycogen at 11.7 T.

The occurrence of a glycogen NOE with water was first confirmed by saturation transfer experiments in vitro. FIGS. 2A-2E show the glycoNOE signal in vitro for liver glycogen. In FIG. 2A, the chemical structure and proton assignment of glycogen is shown. In FIG. 2B, a one-dimensional $^1$H NMR spectrum of bovine liver glycogen is shown (100 mM, pH 7.4, peak assignments are based on the work by L.-H. Zang et al. (30)). The $^1$H MR spectrum shows the spectral positions of glycogen aliphatic protons (assigned in FIG. 2A) relative to water. In FIG. 2C, corresponding signals are observed in the Z-spectra for bovine and rabbit glycogen solutions (300 mM glucose unit, pH 7.4, 20° C.) The bottom row of FIG. 2C shows the residual signal after subtracting out the fitted direct water saturation signal from the Z-spectra.

At the positive frequency offset in FIG. 2C, a broad saturation curve is visible from +0.3 ppm to about +1.5 ppm, a characteristic of intermediate to fast chemical exchange between water and glycogen hydroxyl protons (glycoCEST), which resonate at +0.7 ppm and +1.2 ppm (22). The H1-4 proton at +0.6 ppm is also expected to generate an NOE (27), but at pH 7.4 (as in FIG. 2C) this NOE is hidden under the stronger glycoCEST effect and water direct saturation. The H1-4 NOE peak starts to become visible when glycoCEST effects are small at low pH or high pH (see FIG. 8). In the negative frequency range of Z-spectra, both rabbit and bovine liver glycogen show NOE peaks between −0.6 ppm and −1.5 ppm, which are attributed to a combination of glycogen aliphatic protons H3, H5, and H2+H4-1 (FIGS. 2A-2C) based on previously published assignments in MR spectra (27, 30). At a magnetic field of 11.7 T, these combined signals appear as a single broad peak at approximately −1 ppm, while two composite peaks (at −0.7 ppm and −1.0 ppm) are visible at 17.6 T (see FIG. 5), corresponding to H3 (−0.7 ppm) and the overlapping resonances of H5 (−0.9 ppm) and H2+H4-1 (−1.1 ppm). Interestingly, the rabbit liver glycogen sample (with an average particle size of ~52 nm, see FIG. 6) generates a much stronger NOE signal than the bovine liver glycogen (~7 nm) (as in FIG. 2C), suggesting the glycoNOE signal increases with glycogen particle size, in line with the expectation of stronger NOE with slower motion.

To characterize the glycoNOE signal, rabbit liver glycogen Z-spectra were acquired in vitro as a function of concentration and pH, and at two temperatures (20° C. and 37° C.). In FIG. 2D, the bovine liver glycogen and rabbit liver glycoNOE signals (peak value at −1.0 ppm) are shown as a function of glucose-unit concentration in vitro (pH=7.4, 20° C.). In FIG. 2E, the rabbit liver glycogen (100 mM) NOE signal (peak value) is shown as a function of pH in vitro at 20° C. and 37° C. All data in FIGS. 2A-2E were acquired with a RF saturation strength ($B_1$)=1.0 μT.

Figure 7:
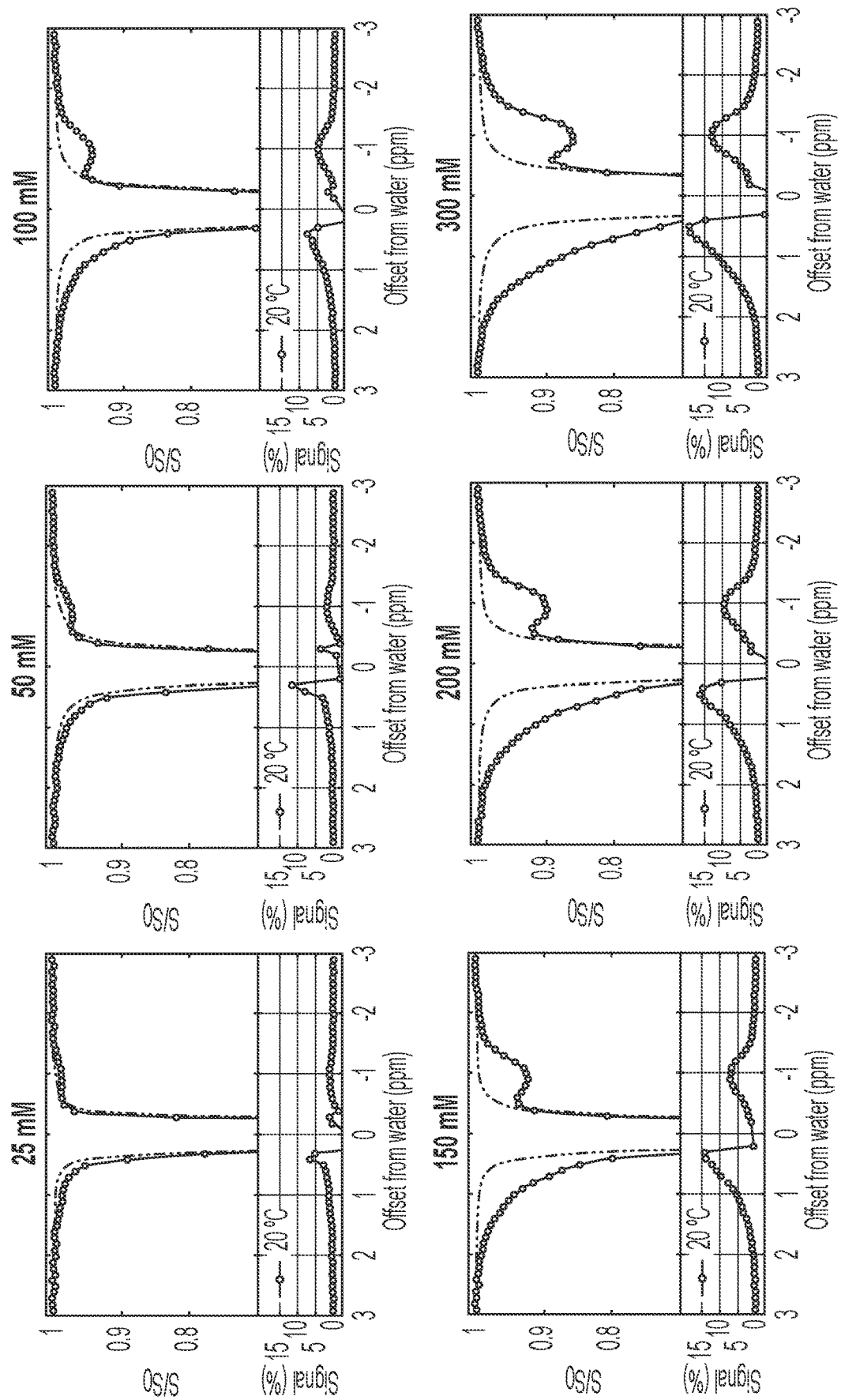
FIG. 7 shows Z-spectra of rabbit liver glycogen at different concentrations in vitro at 11.7 T (500 MHz).
Figure 8:
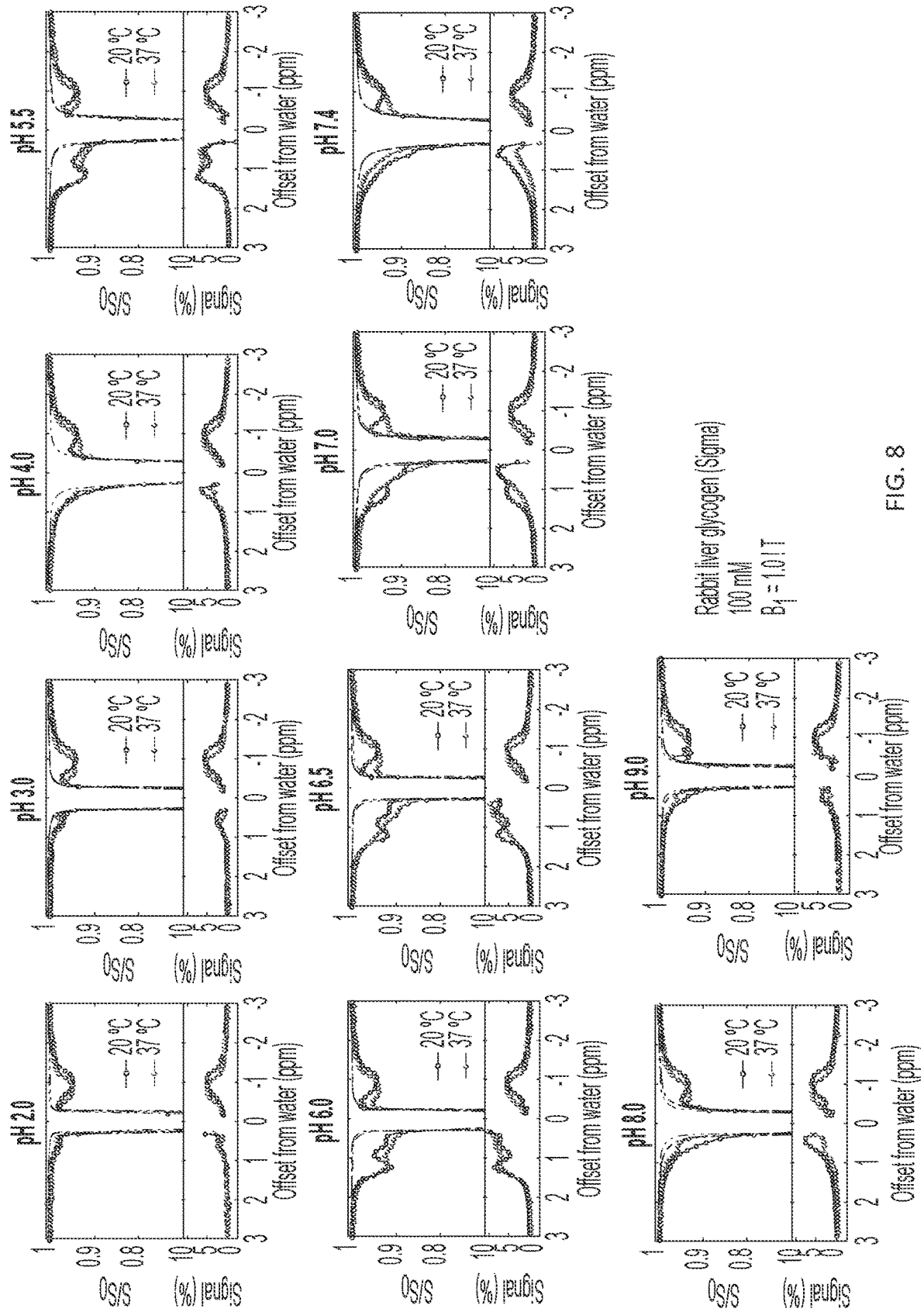
FIG. 8 shows Z-spectra of rabbit liver glycogen (100 mM) as a function of pH at 20° C. and 37° C. in vitro at 11.7 T.

The glycoNOE signal intensity was found to be linearly dependent on concentration (FIG. 2D and also see FIG. 7) and showed negligible dependence on pH and temperature (FIG. 2E and also see FIG. 8). Importantly, these dependencies are in strong contrast with glycoCEST signals (+0.7 ppm and +1.2 ppm) which depend on concentration nonlinearly (21), and are sensitive to pH and temperature (see FIGS. 7, 8). Both glycoNOE and glycoCEST show large signal enhancement ratios: for the 100 mM (equivalent concentration of glucose units) rabbit liver glycogen sample, the glycoNOE peak reaches an intensity equivalent to about 5.3 M proton signal (FIG. 2E, calculated from water percentage), while the glycoCEST effect reaches up to 10 M (see FIG. 8) proton signal depending on pH and temperature.

Figure 3A:
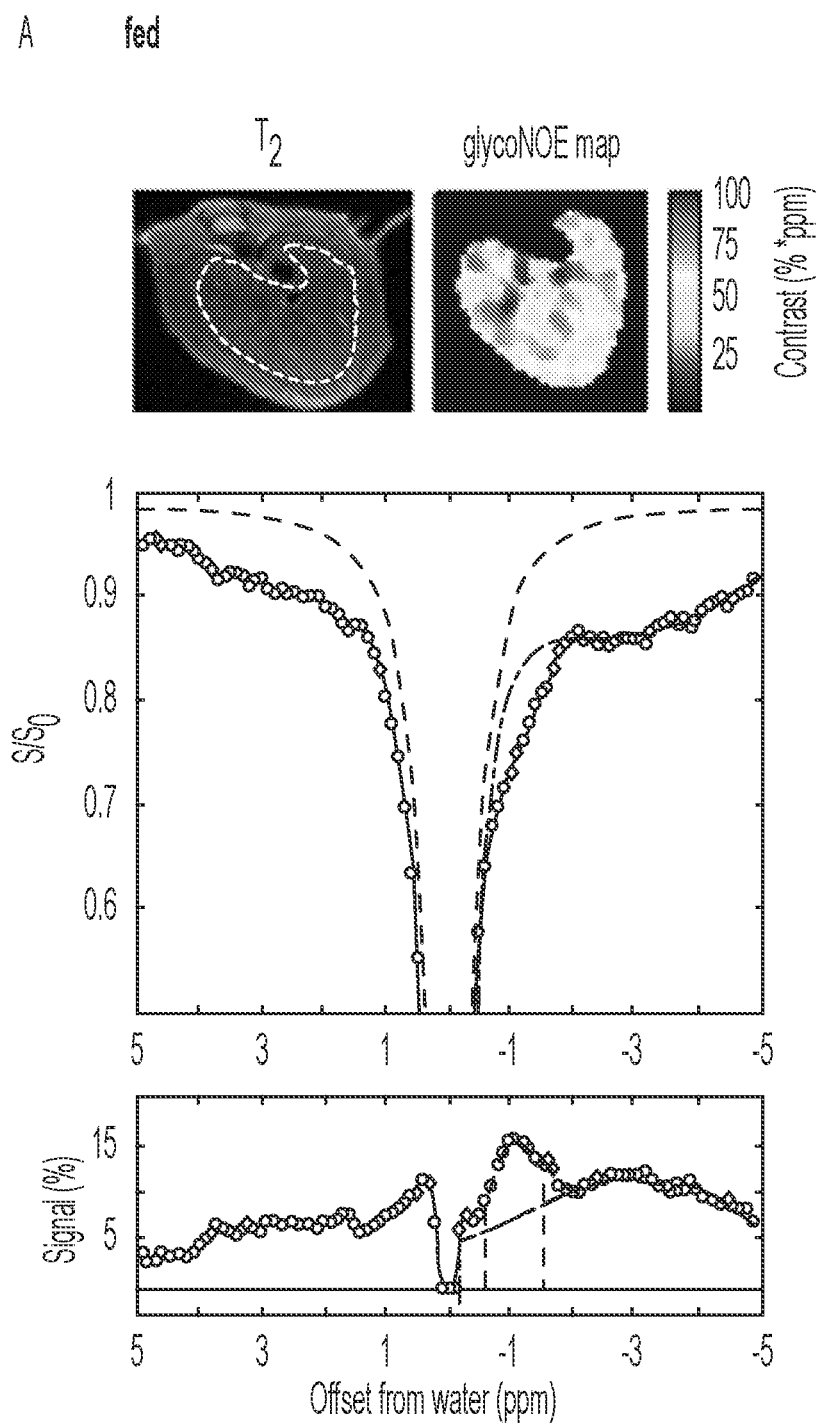
FIGS. 3A and 3B show the effect of fasting on the Z-spectrum from the liver of a healthy mouse at 11.7 T (500 MHz).
Figure 3B:
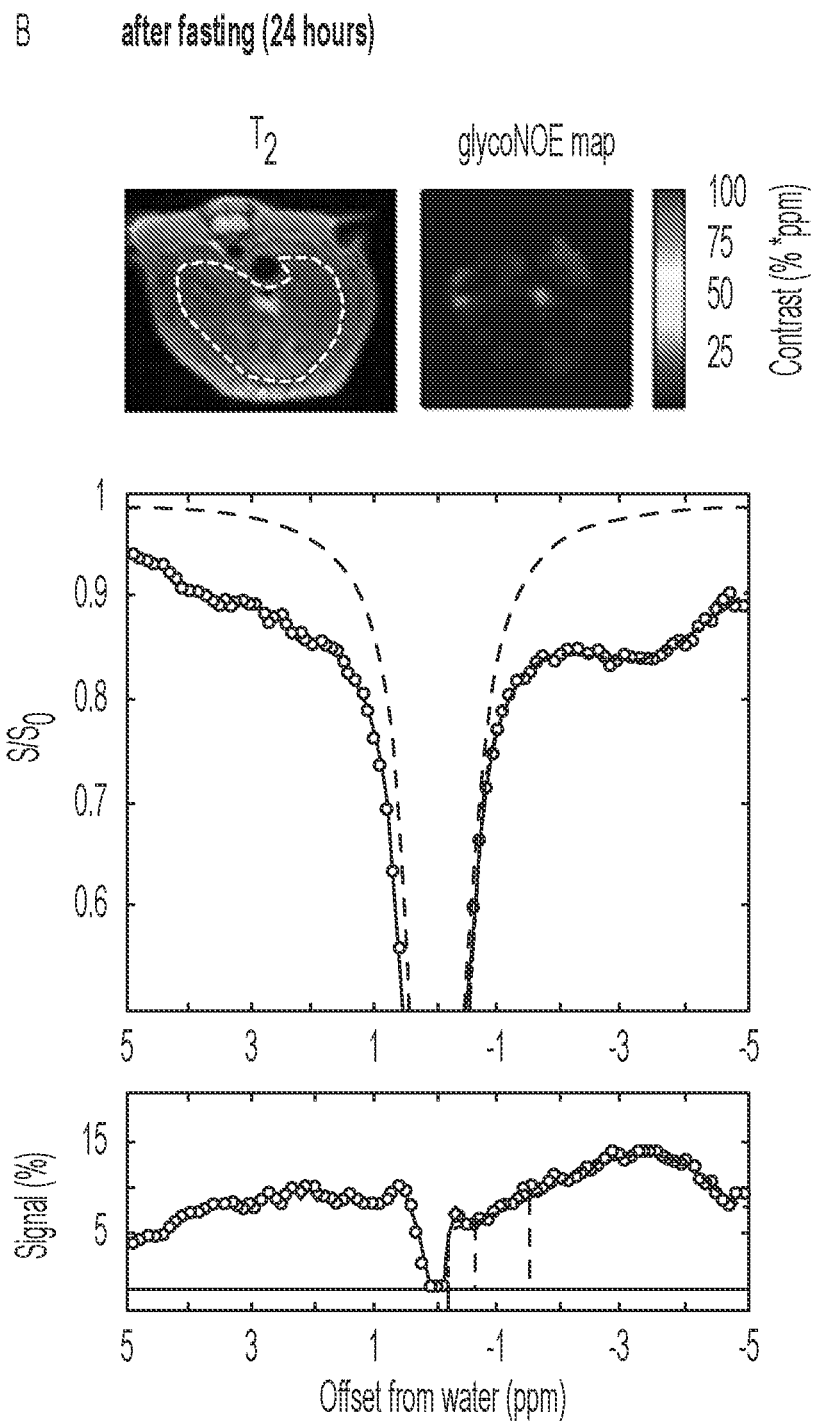

Following the in vitro experiments, glycoNOE experiments were performed in vivo in mouse liver. FIGS. 3A and 3B show the effect of fasting on the Z-spectrum from the liver of a healthy mouse. The same mouse was scanned before (FIG. 3A) and after 24 hours fasting (FIG. 3B). Data was acquired with a RF saturation strength of $B_1$=1.0 μT. The glycoNOE maps were estimated from the voxel-wise integral (unit: %*ppm, which is % times ppm range) of the glycoNOE peak over the shaded area (−0.6 ppm to −1.5 ppm range). The bottom row shows residual Z-spectral signal after subtracting the fitted baseline.

Noticeably, there is a peak at approximately −1 ppm, which is tentatively attributed to the overlapped NOE peaks from glycogen protons H3, H5, and H2+H4-1 and assigned to be the glycoNOE peak. To estimate the glycoNOE peak intensity in vivo, the smooth part of the negative range (−0.1 ppm to −8 ppm) of the Z-spectrum was fitted using a multi-Lorentzian approach (31) and the magnetization transfer background was subtracted from the experimental data. The residual signal (bottom panel of FIG. 3A) shows overlapping peaks from different origins in the liver. The glycoNOE peak intensity was quantified by taking the integral from −0.6 ppm to −1.5 ppm (shaded area in FIG. 3A). The glycoNOE maps (top row of FIGS. 3A and 3B, also see FIGS. 9, 11-14) generated using this approach on a voxel-by-voxel basis, show a heterogeneous distribution of glycogen over the liver.

Figure 16:
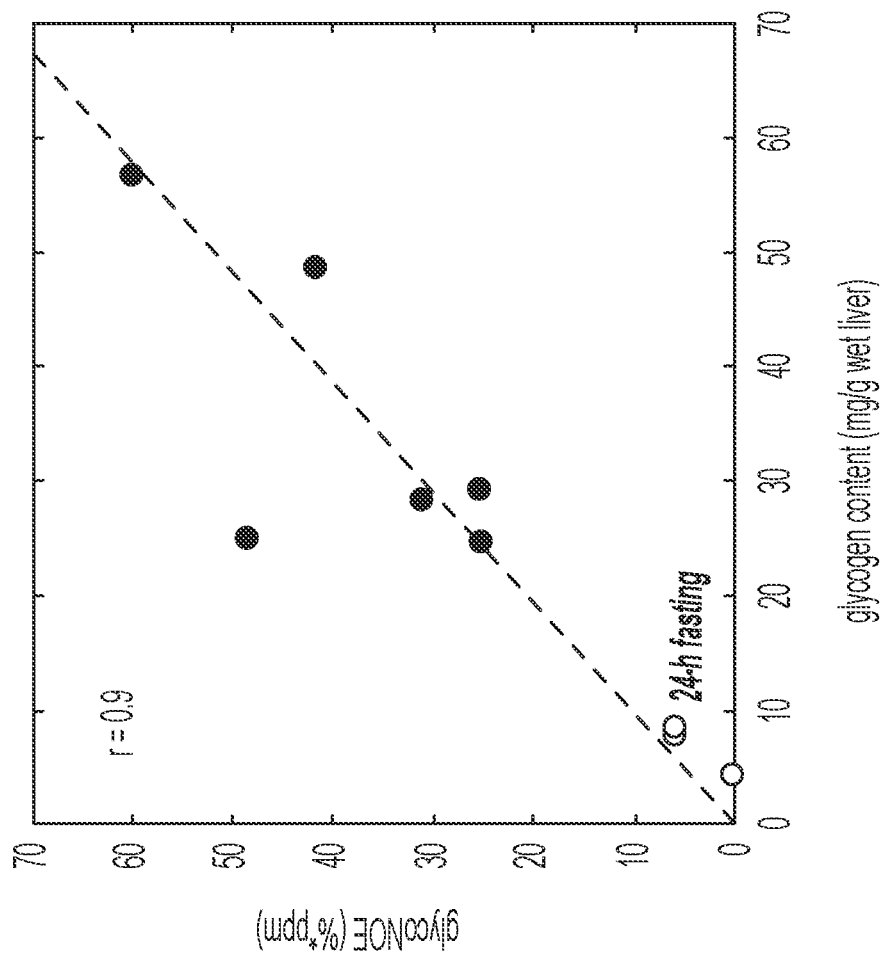
FIG. 16 shows the relationship between GlycoNOE signal ($B_1$=1.0 at 11.7 T) and the glycogen content measured in the liver using a chemical assay.

To calibrate the glycoNOE signal with liver glycogen content, mouse liver glycogen was immediately extracted and quantified after glycoNOE MRI. The average glycoNOE signal was found to be linearly correlated with measured glycogen content (FIG. 16). To further confirm the origin of the glycoNOE signal in liver, glycogen depletion experiments were performed using (a) a 24-hour fasting protocol, or (b) glucagon injections. The liver Z-spectra for mice in the fasted state show that the glycoNOE peak is greatly depleted (FIG. 3B, and FIGS. 11-15). For five mice studied after fasting for 24-28 hours, the integrated liver glycoNOE signal (−0.6 ppm to −1.5 ppm) decreased on average from 49±8%*ppm (equivalent to a glycogen concentration of about 47 mg/g wet liver; signal unit: % times ppm range) at fed state to 6±8%*ppm (~6 mg/g) in the fasted state (N=5).

Glucagon injection experiments were also conducted to induce a change of glycogen level in mouse liver. Glucagon accelerates liver glycogen breakdown, thus allowing the monitoring of glycogen depletion within two hours. FIGS. 4A-4F and FIGS. 17-21 show the changes in the liver Z-spectrum as a function of time after intraperitoneal (i.p.) injection of glucagon.

Figures 4A, 4B, 4C, 4D:
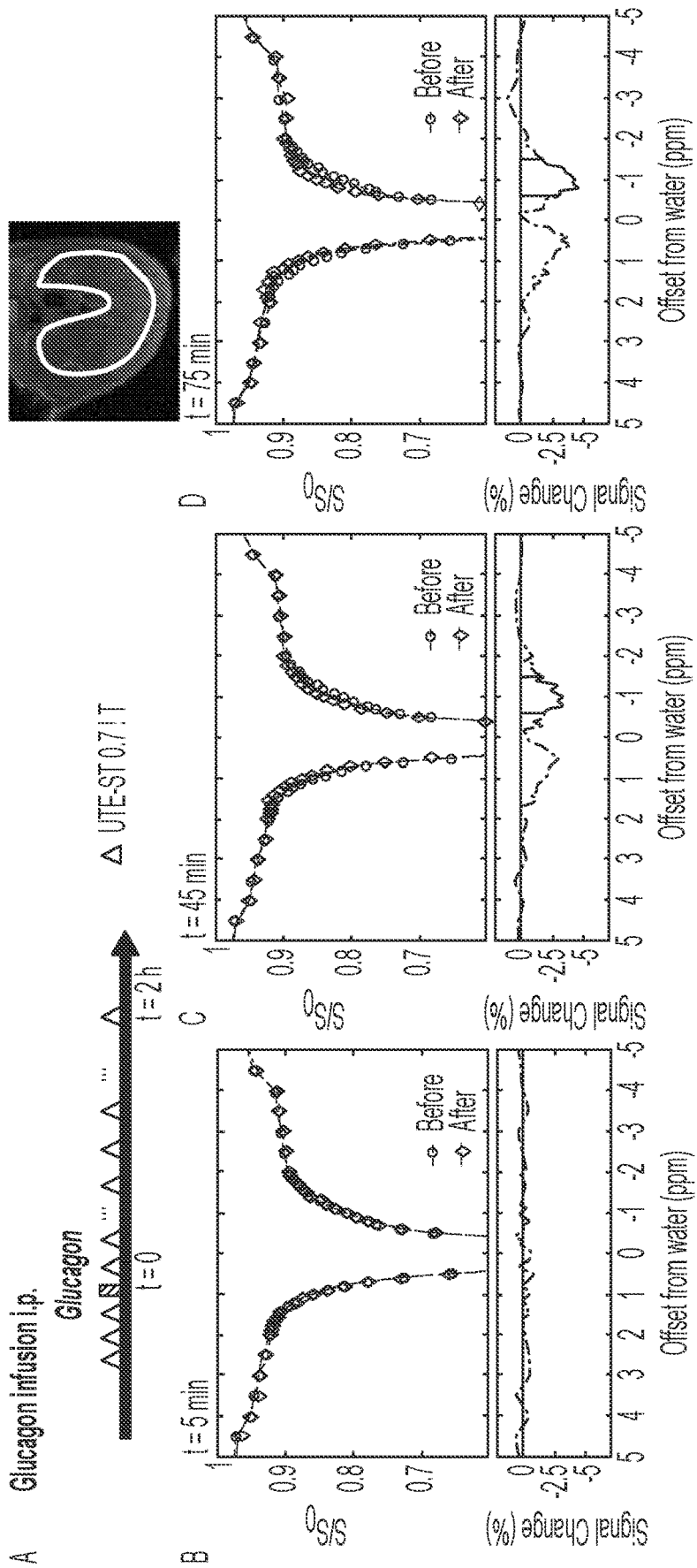
FIGS. 4A-4F show the effects of glucagon on glycoNOE contrast in the liver of fed mice at 11.7 T (500 MHz).
Figures 4E, 4F:
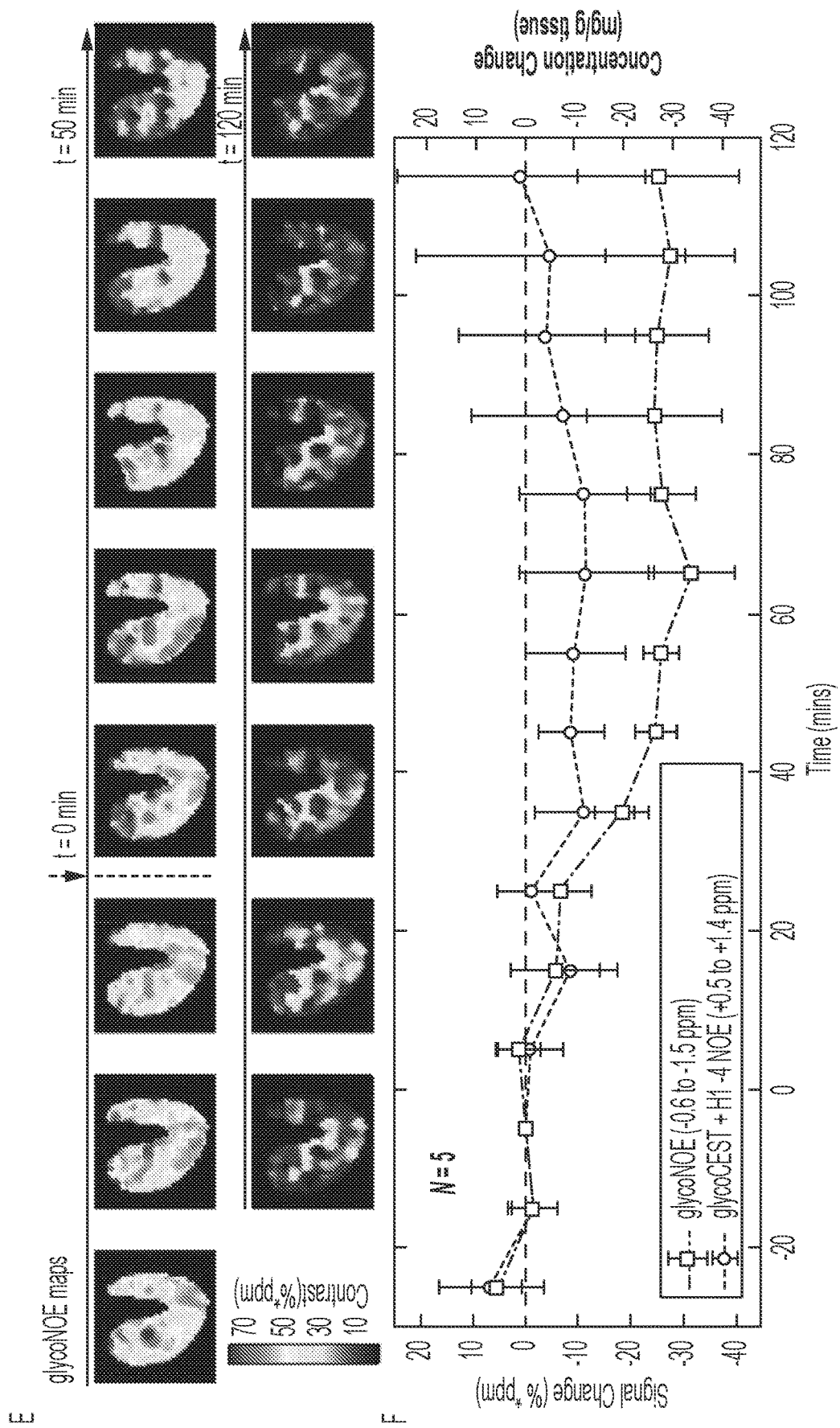

In FIG. 4A, an experimental scheme is shown, an ultra-short echo time saturation transfer (UTE-ST) MRI experiments ($B_1$=0.7 μT) conducted before and after glucagon (100 μl, 1 mg/ml) injection. In FIGS. 4B, 4C, and 4D, Z-spectral changes are shown after glucagon for the indicated ROI. In FIG. 4E, glycoNOE maps are shown as a function of time before and after injection. In FIG. 4F, the average (N=5) glycoNOE and "glycoCEST+H1-4 NOE" signal changes are shown as a function of time in mouse liver. The average glycogen concentration changes (righty axis) were calculated from glycoNOE signal.

The Z-spectral differences between pre- and post-injection show a great reduction of the integrated glycoNOE signal (−0.6 ppm to −1.5 ppm) due to the effect of glucagon (FIGS. 4C and 4D). By fitting the Z-spectra voxel by voxel, glycoNOE maps were constructed at different time points. FIG. 4E shows how the glycoNOE signal in the liver changed spatially with time after glucagon injection. At 65 minutes post injection, the average glycoNOE signal (N=5) in the liver was greatly depleted from 45±15%*ppm (~48 mg/g) to 11±9%*ppm (~12 mg/g). FIG. 4F shows the average (N=5) integrated glycoNOE signal (and corresponding concentration) and "glycoCEST+H1-4 NOE" signal changes as a function of time. The glycoNOE signal reached a stationary phase approximately 60 mins after glucagon injection. The results clearly show that the glycoNOE signal is reduced with the breaking down of hepatic glycogen. There are also signal changes in the region of 0 ppm~+1.5 ppm with a peak of around +0.6 ppm, corresponding to the combined effect of hydroxyl protons (glycoCEST) and the glycogen H1-4 NOE. It is uncertain how much the H1-4 NOE and hydroxyl exchange each contribute to this signal.

Figure 5:
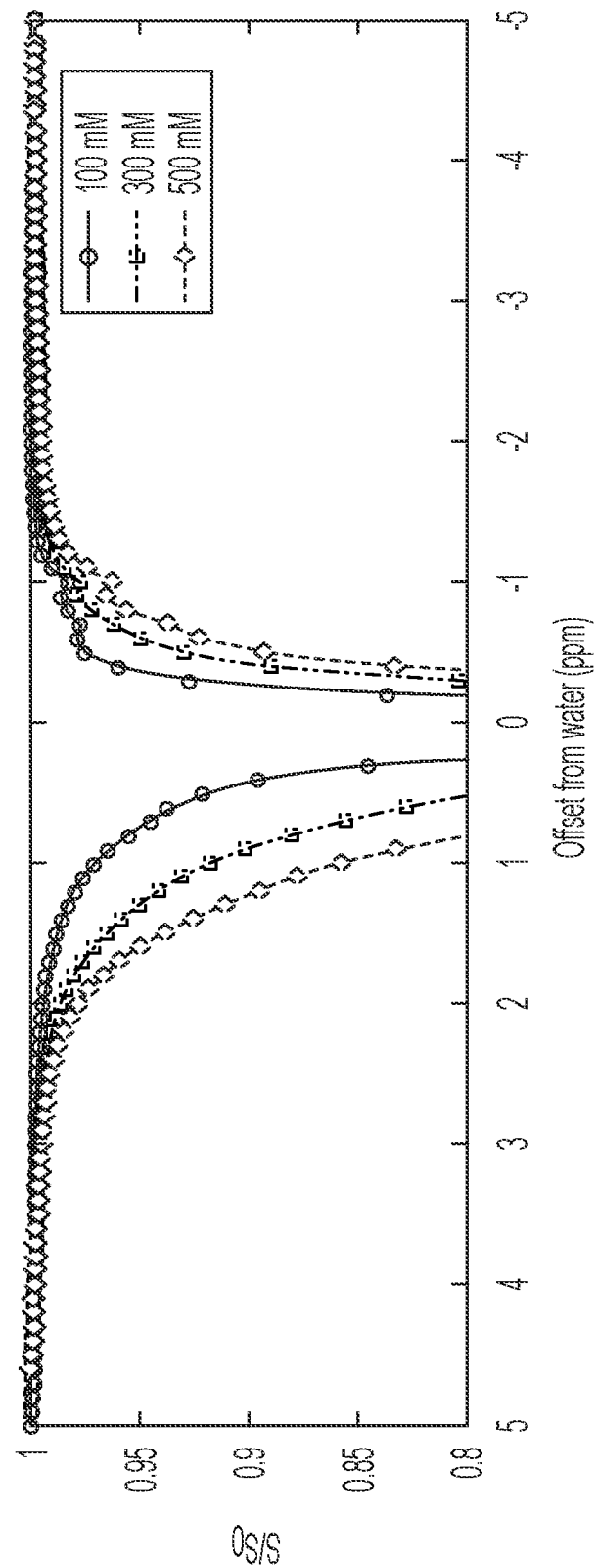
FIG. 5 shows Z-spectra of bovine liver glycogen solutions at 17.6 T (750 MHz).

FIG. 5 shows Z-spectra of bovine liver glycogen solutions at 17.6 T (750 MHz). Each sample contained different concentrations (glucose unit based) of glycogen with 10% $D_2O$ in a 5-mm NMR tube which was scanned in a 17.6 T Bruker Avance III (Bruker, Ettlingen, Germany) at 37° C. Z-spectra were collected using irradiation frequencies from +5 ppm to −5 ppm with 0.1 ppm steps. Saturation labeling of protons was achieved using a 4 s pre-saturation pulse with a $B_1$ strength of 0.37 µT (16 Hz).

Figure 6:
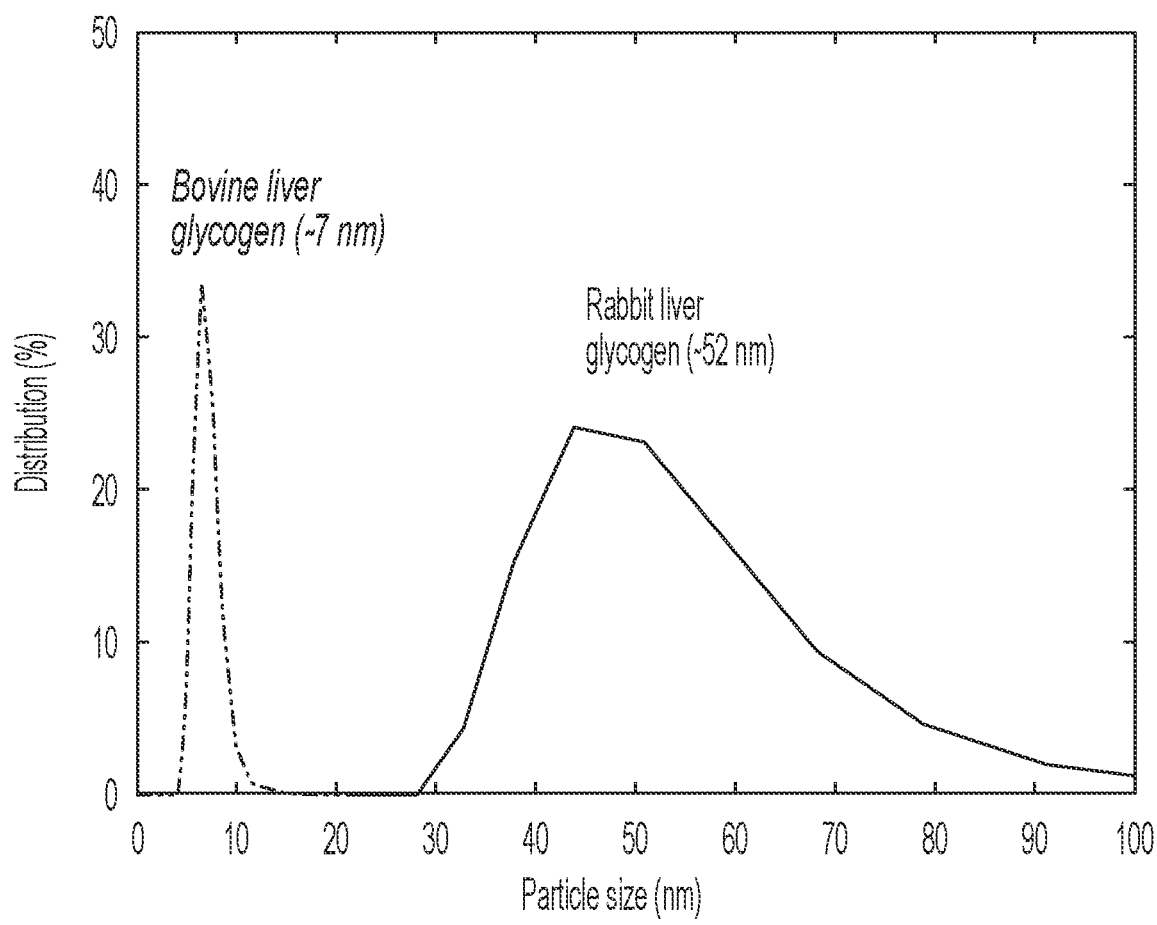
FIG. 6 shows particle size distribution of bovine liver glycogen and rabbit liver glycogen samples.

FIG. 6 shows the particle size distribution of bovine liver glycogen and rabbit liver glycogen samples. Sizes of the commercial samples (Sigma) in PBS were measured using dynamic light scattering (DLS) based zetasizer (Zetasizer Nano ZS90, Malvern Instruments). Note that the size differences of the two samples is likely due to the purification steps at the company instead of real differences that exist in vivo.

FIG. 7 shows Z-spectra of rabbit liver glycogen (pH 7.4) at various different concentrations in vitro at 11.7 T (500 MHz). The concentrations shown are (top row) 25 mM, 50 mM, and 100 mM, and (bottom row) 150 mM, 200 mM, and 300 mM. A UTE-ST pulse sequence with a $B_1$ of 1.0 µT was used.

FIG. 8 shows Z-spectra of rabbit liver glycogen (100 mM) as a function of pH at 20° C. and 37° C. in vitro at 11.7 T. UTE-ST with a $B_1$ of 1.0 µT was used. While the glycoNOE signal intensity is temperature independent, there is a frequency shift between spectra acquired at 20° C. and 37° C., which is tentatively attributed to the dependence of the water frequency on temperature (42) and independence on temperature of the aliphatic protons in glycogen. Other signal variations about the water frequency at different temperature and pH are likely due to changes in the glycoCEST effect which is strongly influenced by temperature and pH (see above). The close proximity of the water (0 ppm) and glycoCEST signals (extending on both sides of the water signal due to the intermediate-fast exchange conditions) to the glycoNOE peak region (−1 ppm) means that any changes in these signals may influence the glycoNOE peak appearance. However, after fitting, the residual signals (bottom of the figure panels) show negligible effects of temperature and pH on glycoNOE signal intensity.

Figure 10:
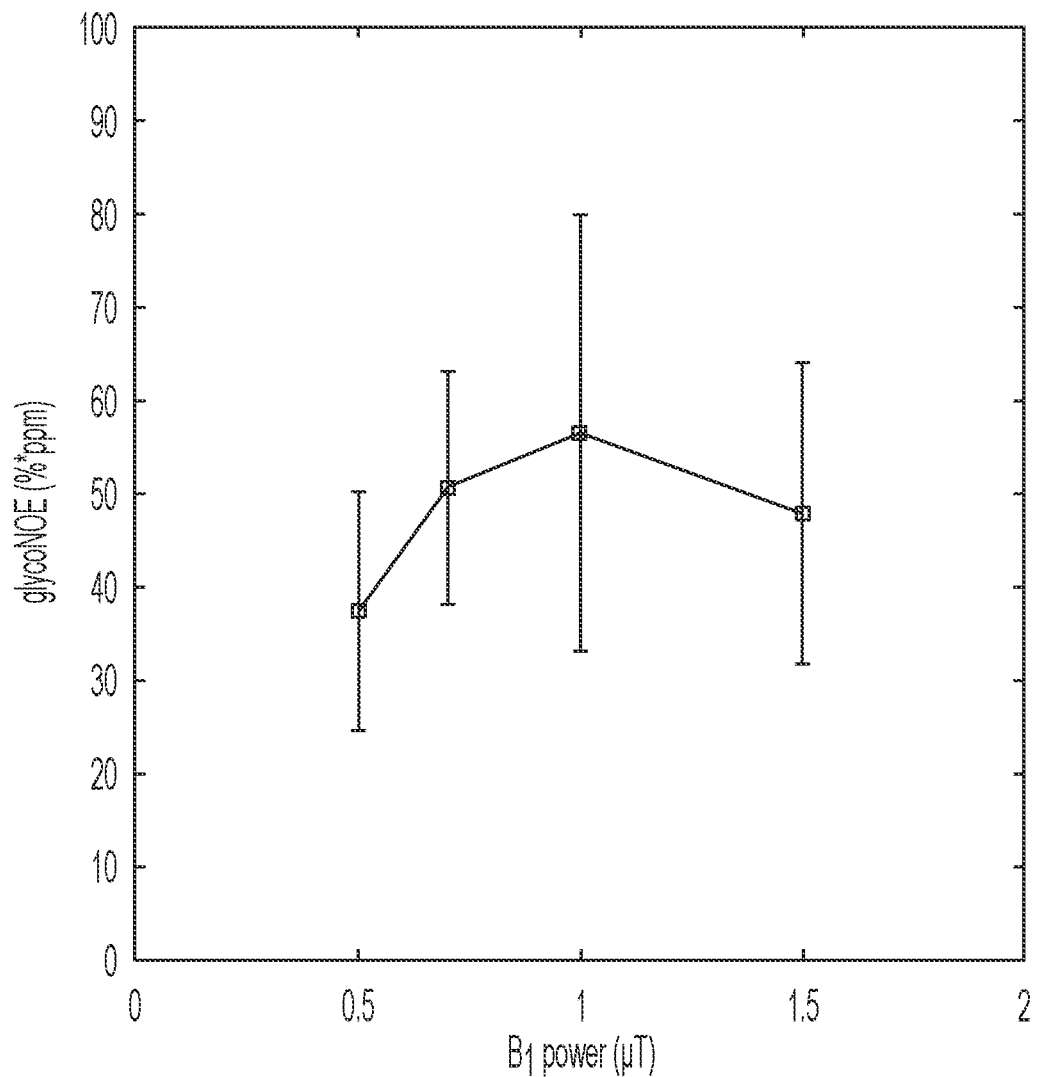
FIG. 10. illustrates the dependence of glycoNOE signal (integral) in fed mouse liver on $B_1$ strength at 11.7 T.
Figure 11:
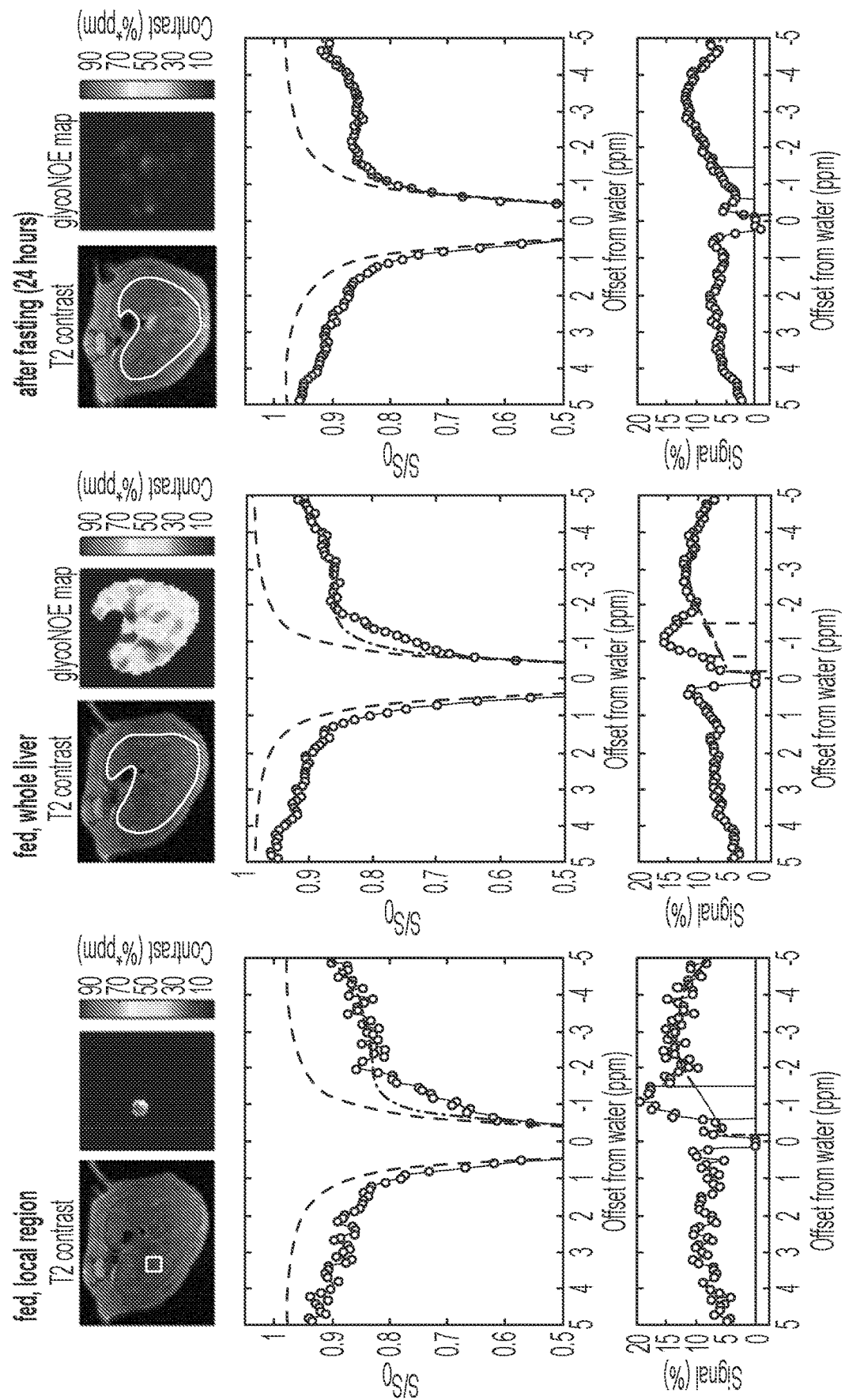
FIG. 11 shows Z-spectra ($B_1$=1.0 µT) for fed and fasted liver in a first mouse subject at 11.7 T.
Figure 12:
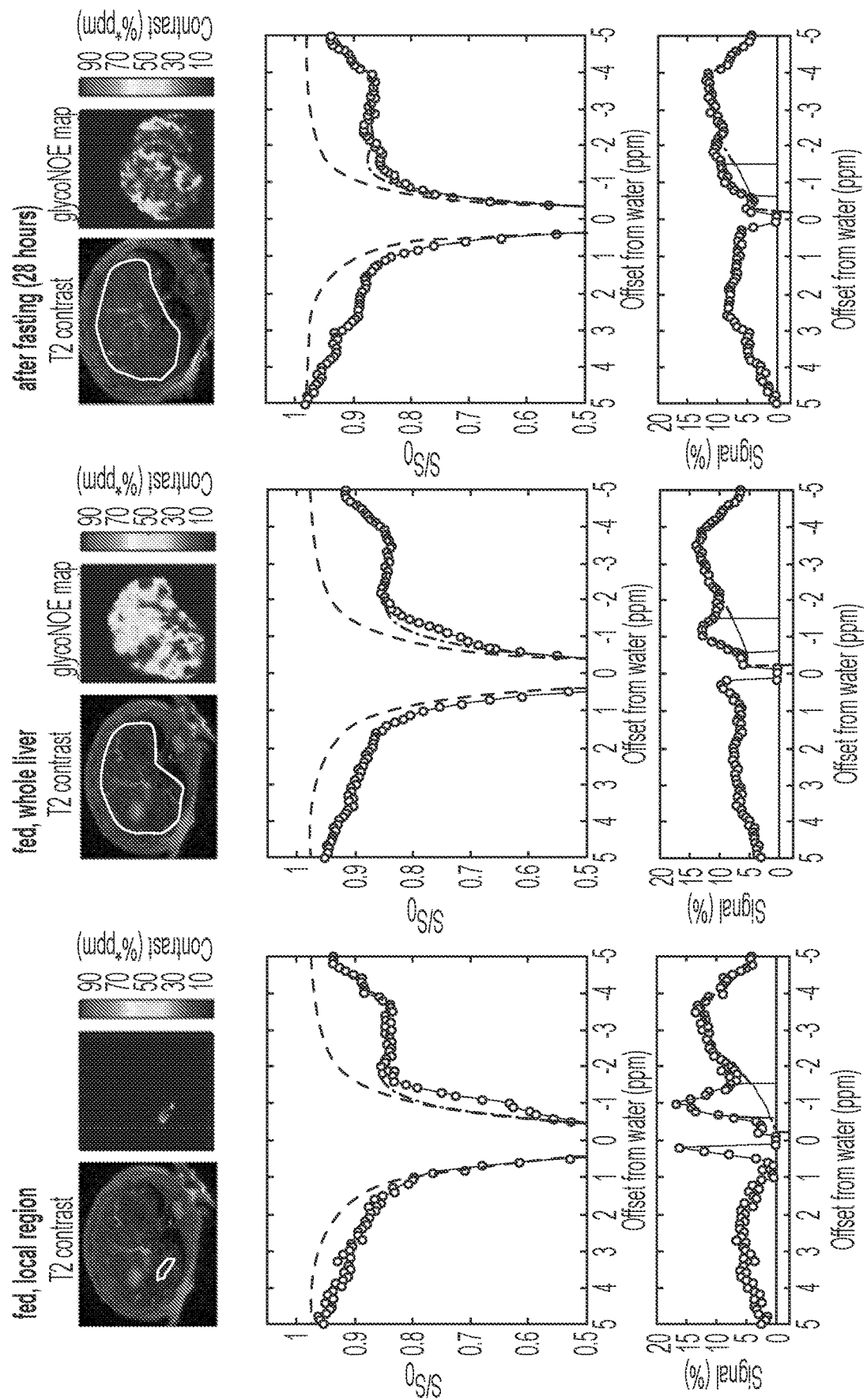
FIG. 12 shows Z-spectra ($B_1$=1.0 µT) for fed and fasted liver in a second mouse subject at 11.7 T.
Figure 13:
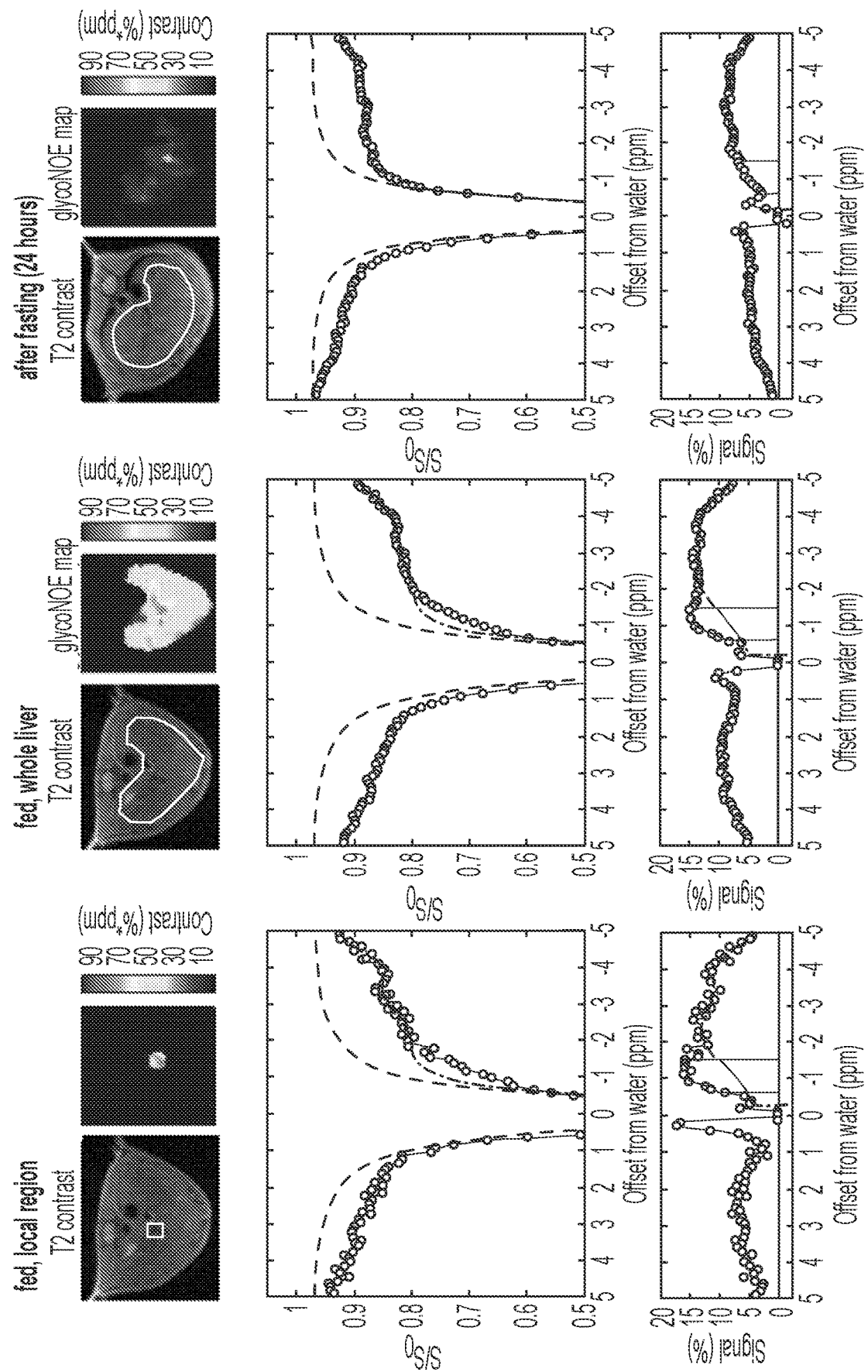
FIG. 13 shows Z-spectra ($B_1$=1.0 µT) for fed and fasted liver in a third mouse subject at 11.7 T.
Figure 14:
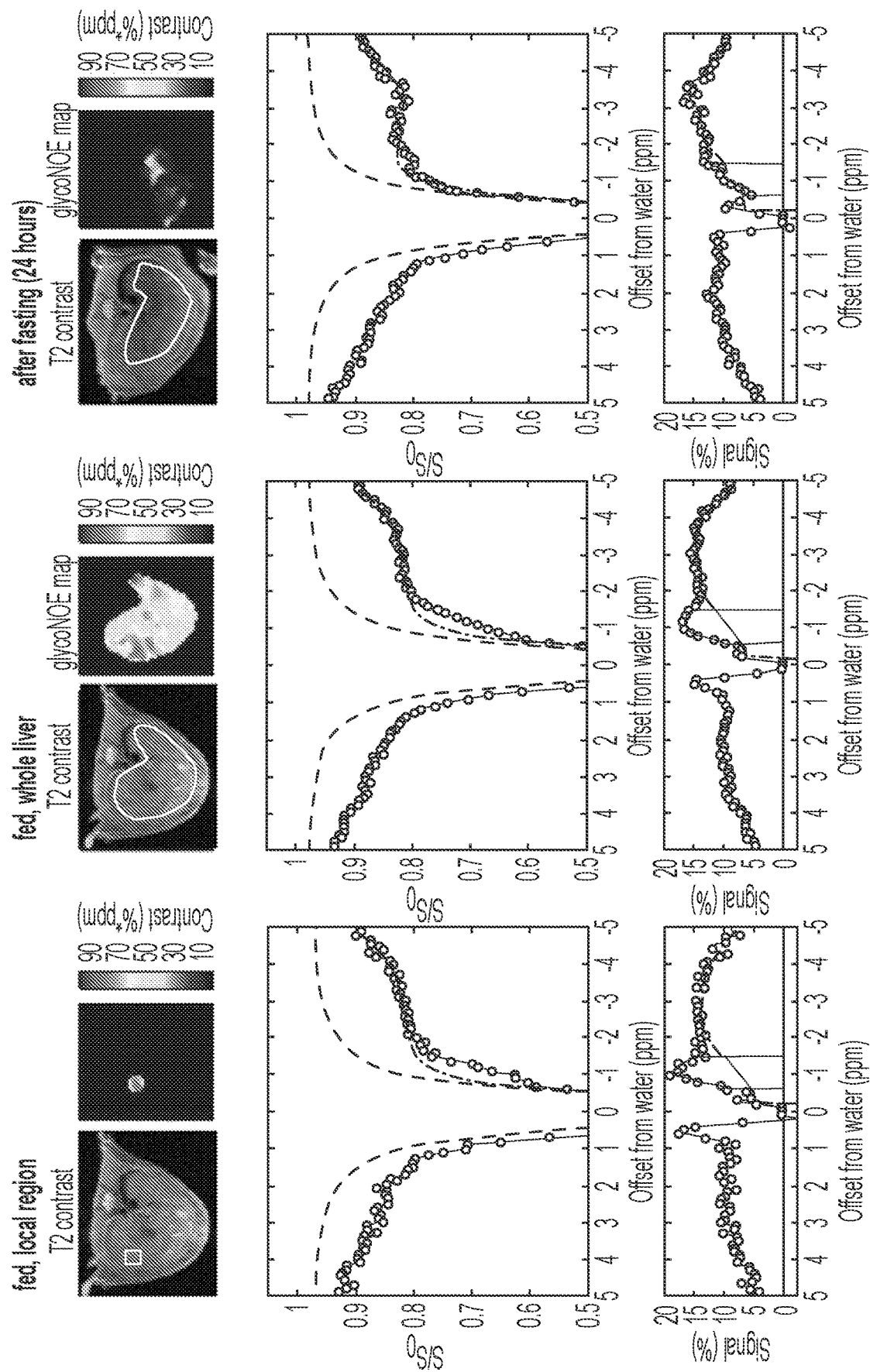
FIG. 14 shows Z-spectra ($B_1$=1.0 µT) for fed and fasted liver in a fourth mouse subject at 11.7 T.
Figure 15:
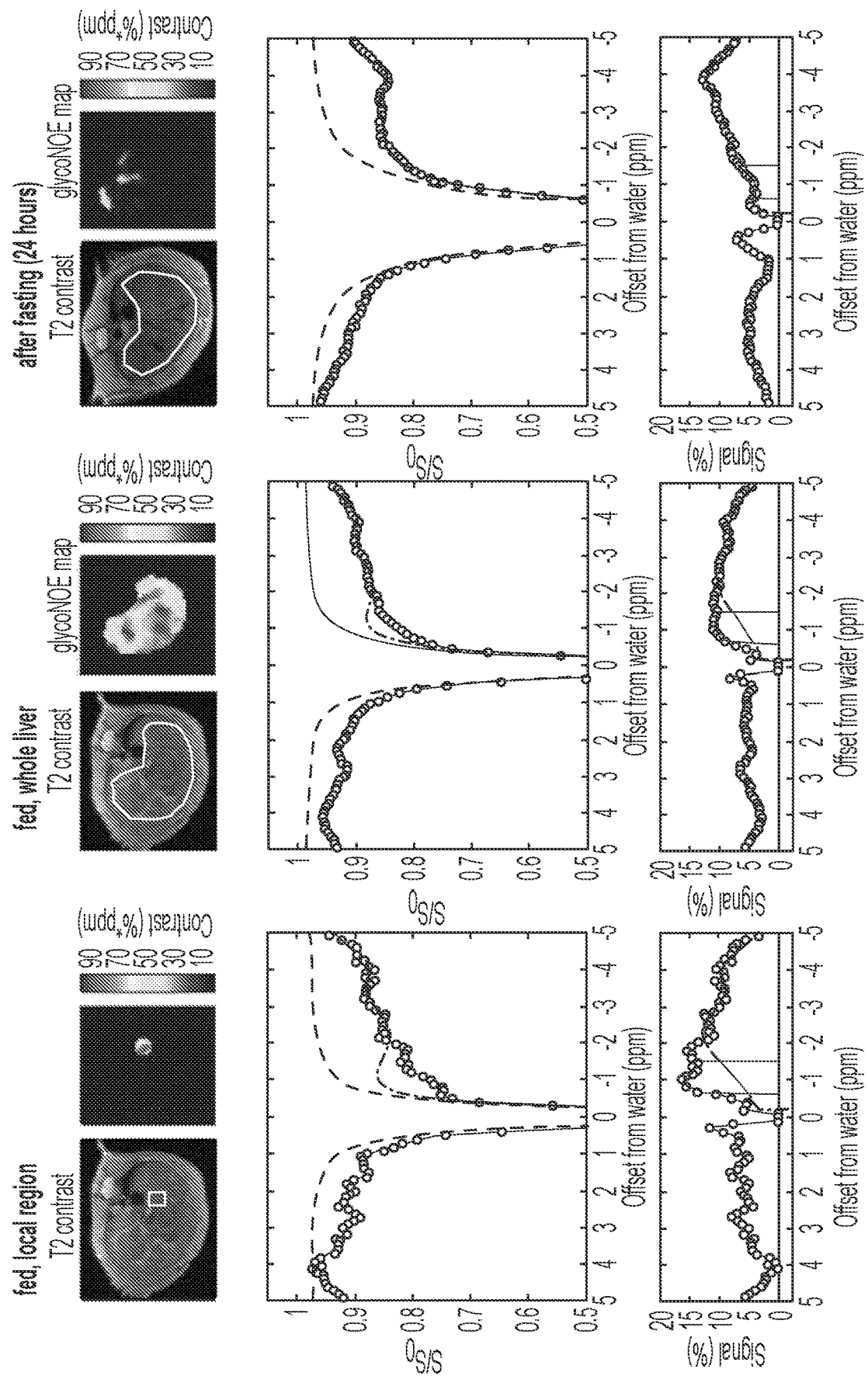
FIG. 15 shows Z-spectra ($B_1$=1.0 µT) for fed and fasted liver in a fifth mouse subject at 11.7 T.

FIGS. 9A-9D show anatomical (FIG. 9A) and glycoNOE maps of a fed mouse liver with $B_1$ of 0.5 µT (FIG. 9B), 1.0 µT (FIG. 9C) and 1.5 µT (FIG. 9D). FIG. 10. illustrates the dependence of glycoNOE signal (integral) in fed mouse liver on $B_1$ (N=7). FIGS. 11 to 15 show Z-spectra ($B_1$=1.0 µT) for fed liver (local region), fed liver (whole liver), and fasted liver in mouse subjects one through five. FIG. 16 shows the glycoNOE signal ($B_1$=1.0 µT) and the glycogen content measured using a chemical assay.

Figures 17A, 17B, 17C, 17D:
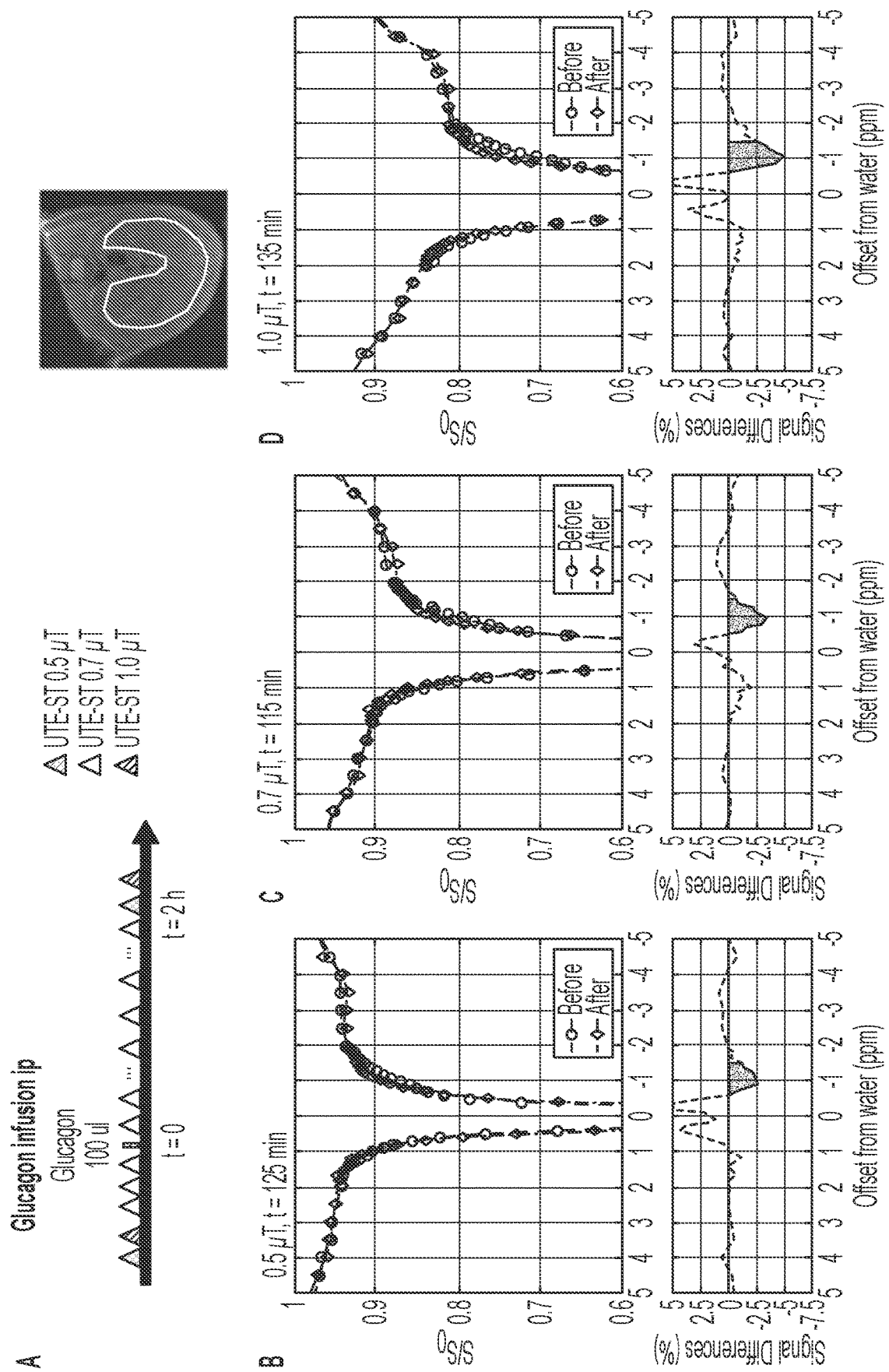
FIGS. 17A-17D illustrate how the glycoNOE signal changes due to glucagon after approximately two hours for three different $B_1$ strengths in a sixth mouse subject at 11.7 T.

FIGS. 17A-17D illustrates how the glycoNOE signal changes due to glucagon after approximately two hours for three different $B_1$ levels (mouse subject six). FIG. 17A shows the UTE-ST pulse sequence at $B_1$ strengths of 0.5 µT, 0.7 µT, and 1.0 µT. In FIGS. 17B to 17D, the $B_1$ dependence for signal difference is shown after approximately two hours for each $B_1$, 0.5 µT (FIG. 17B), 0.7 µT (FIG. 17C), and 1.0 µT (FIG. 17D).

Figures 18A, 18B, 18C, 18D:
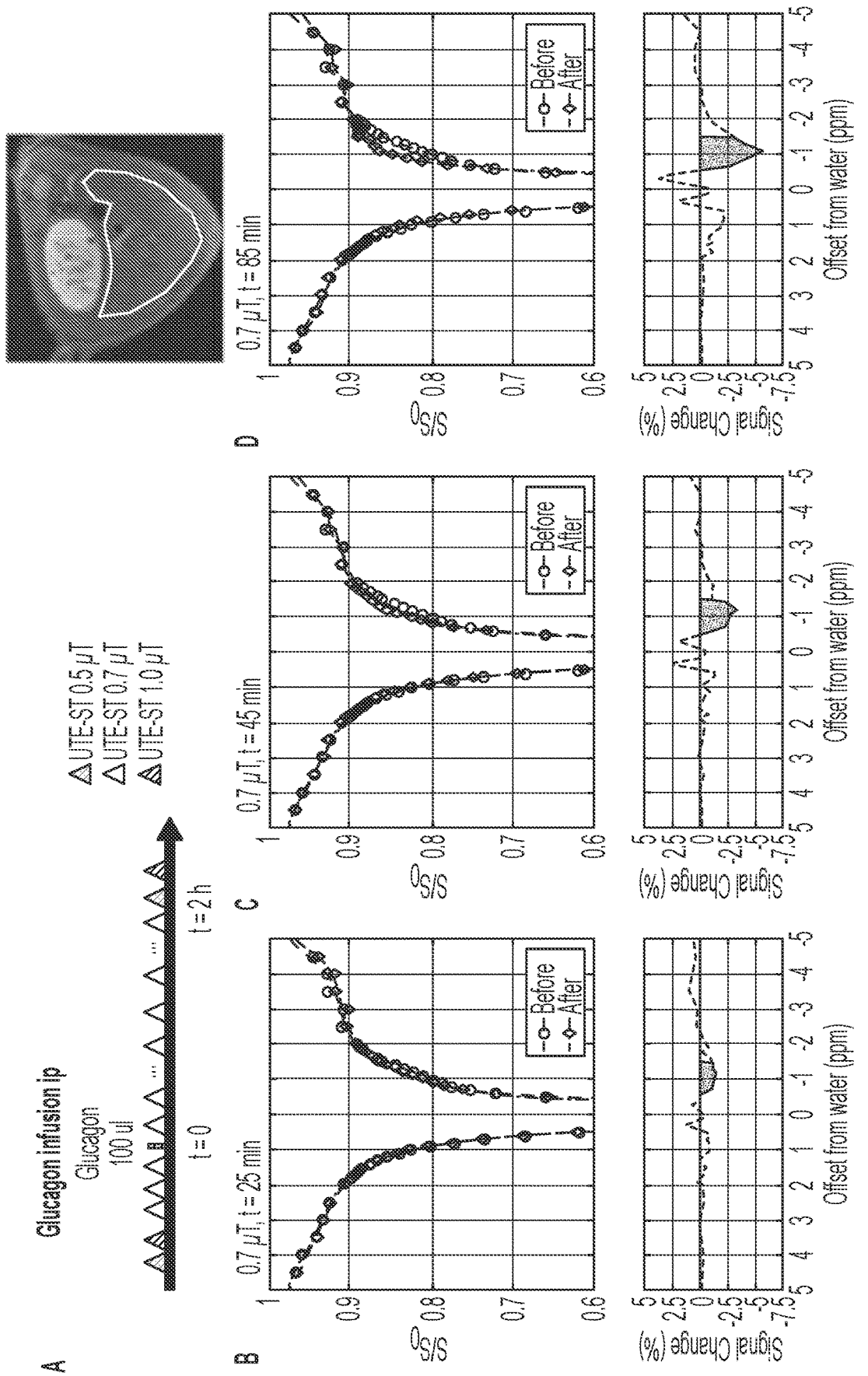
FIGS. 18A-18G show the effect of glucagon on mouse liver Z-spectra in a seventh mouse subject at 11.7 T.
Figures 18E, 18F, 18G:
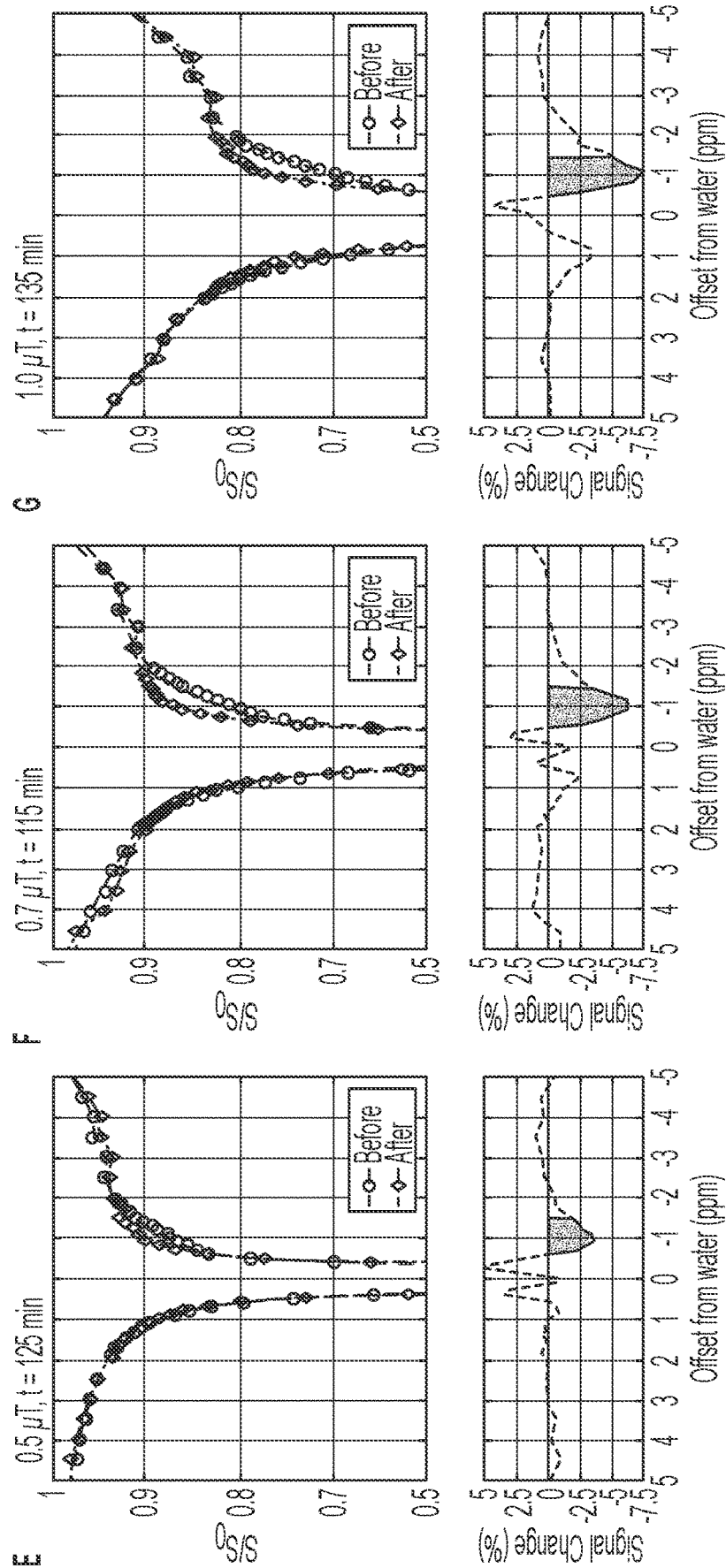

FIGS. 18A-18G show the effect of glucagon on mouse liver Z-spectra (mouse subject seven). FIG. 18A shows the UTE-ST pulse sequence at $B_1$ strengths of 0.5 µT, 0.7 µT, and 1.0 µT. In FIGS. 18B-18D, the time dependence after injection at $B_1$=0.7 µT is shown, at 25 minutes (FIG. 18B), 45 minutes (FIG. 18C), and 85 minutes (FIG. 18D). In FIGS. 18E to 18G, the $B_1$ dependence for signal difference is shown before injection and after approximately two hours for each $B_1$, 0.5 µT (FIG. 18E), 0.7 µT (FIG. 18F), and 1.0 µT (FIG. 18G).

Figures 19A, 19B, 19C, 19D:
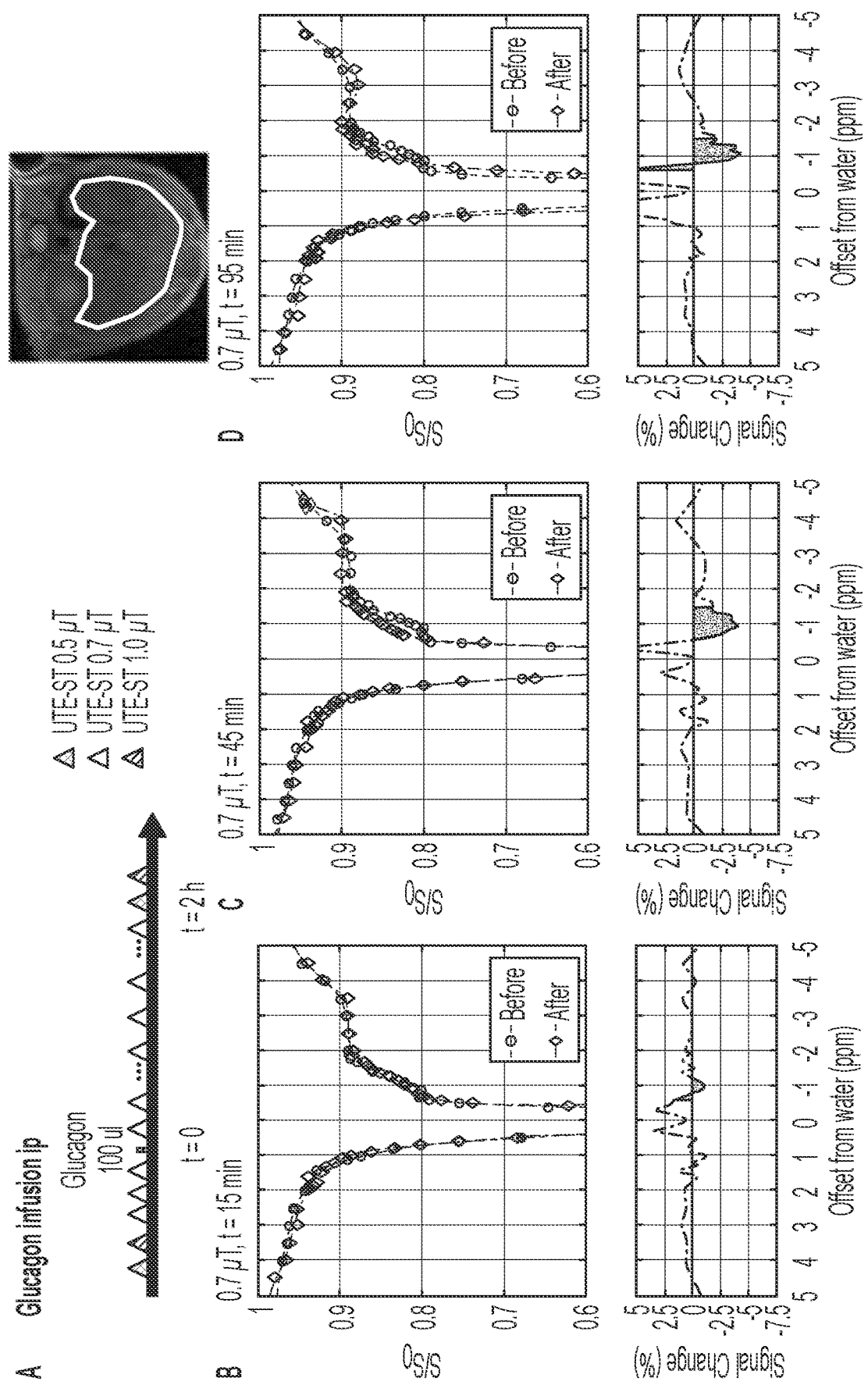
FIGS. 19A-19G show the effect of glucagon on mouse liver Z-spectra in an eighth mouse subject at 11.7 T.
Figures 19E, 19F, 19G:
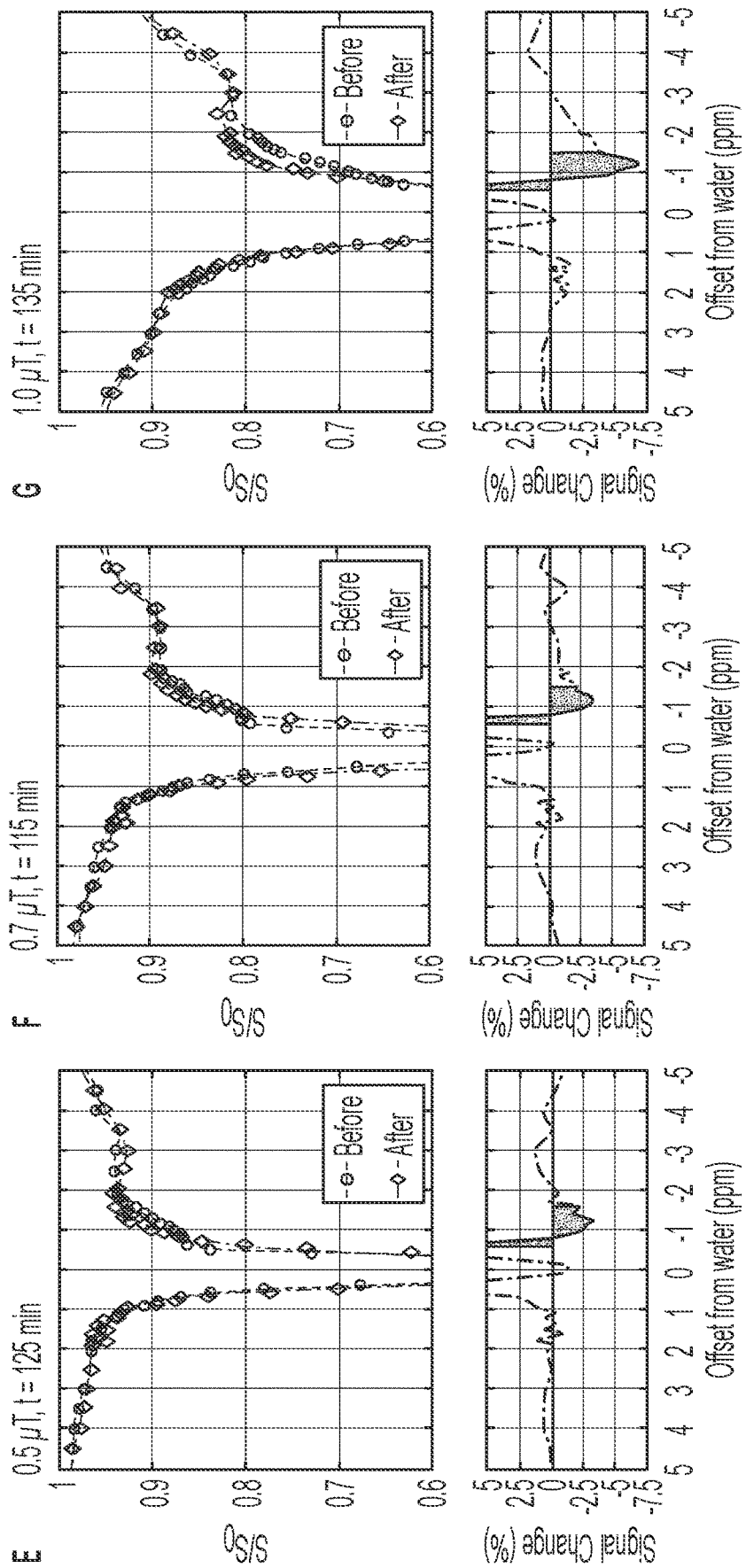

FIGS. 19A-19G show the effect of glucagon on mouse liver Z-spectra (mouse subject eight). FIG. 19A shows the UTE-ST pulse sequence at $B_1$ strengths of 0.5 µT, 0.7 µT, and 1.0 µT. In FIGS. 19B-19D, the time dependence after injection at $B_1$=0.7 µT is shown, at 15 minutes (FIG. 19B), 45 minutes (FIG. 19C), and 95 minutes (FIG. 19D). In FIGS. 19E to 19G, the $B_1$ dependence for signal difference is shown before injection and after approximately two hours for each $B_1$, 0.5 µT (FIG. 19E), 0.7 µT (FIG. 19F), and 1.0 µT (FIG. 19G).

Figures 20A, 20B, 20C, 20D:
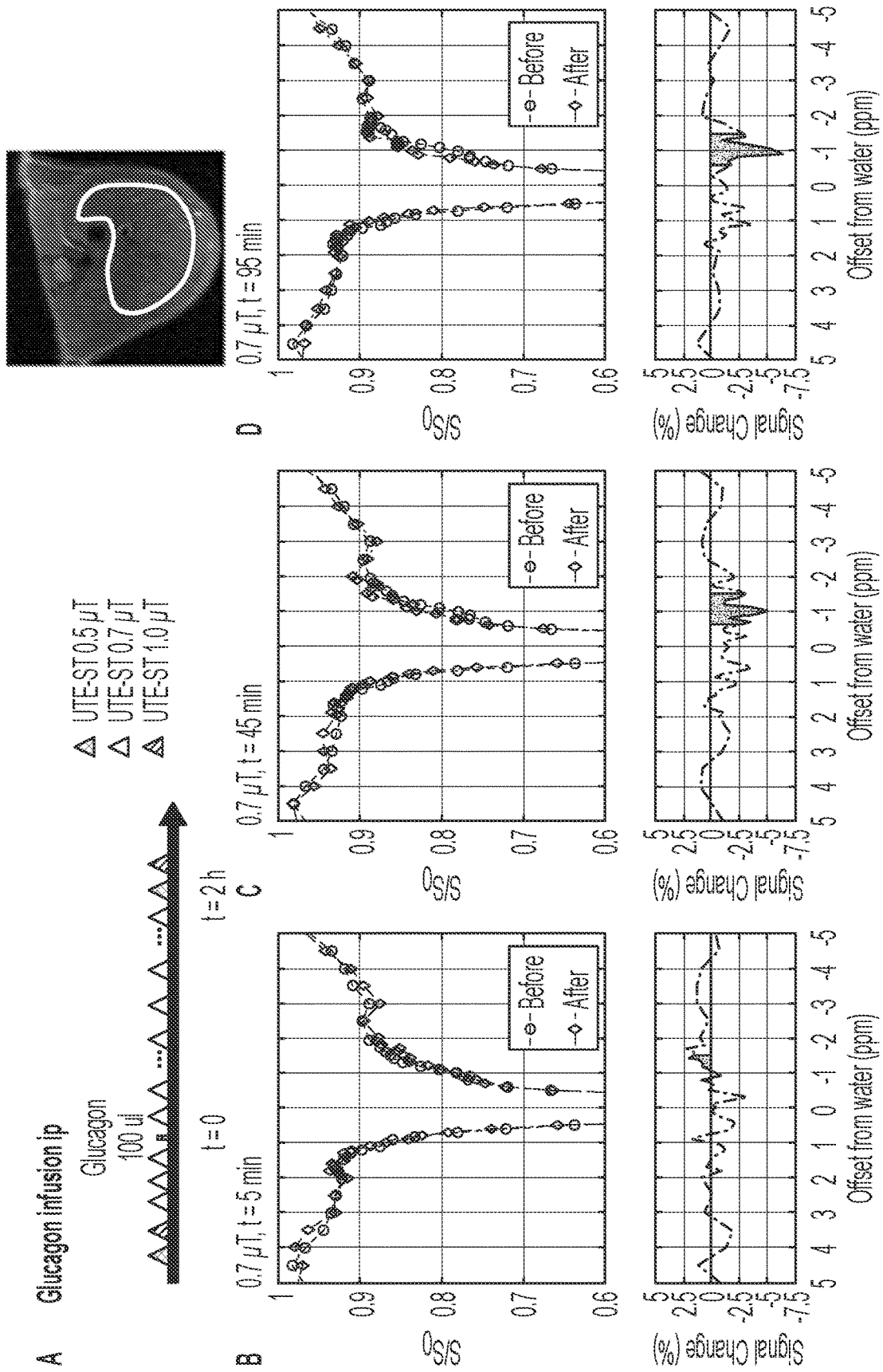
FIGS. 20A-20G show the effect of glucagon on mouse liver Z-spectra in a ninth mouse subject at 11.7 T.
Figures 20E, 20F, 20G:
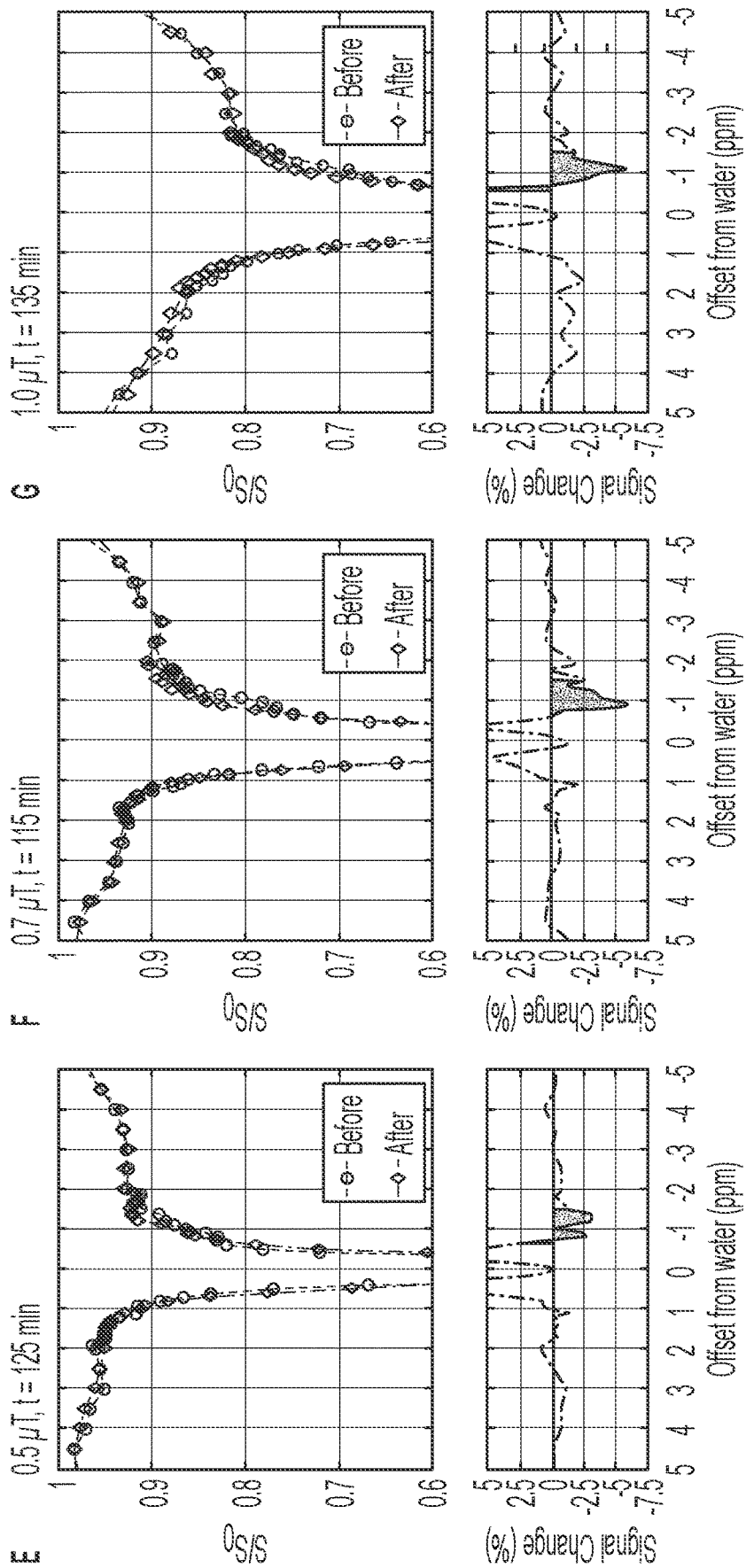

FIGS. 20A-20G show the effect of glucagon on mouse liver Z-spectra (mouse subject nine). FIG. 20A shows the UTE-ST pulse sequence at $B_1$ strengths of 0.5 µT, 0.7 µT, and 1.0 µT. In FIGS. 20B-20D, the time dependence after injection at $B_1$=0.7 µT is shown, at 5 minutes (FIG. 20B), 45 minutes (FIG. 20C), and 95 minutes (FIG. 20D). In FIGS. 20E to 20G, the $B_1$ dependence for signal difference is shown before injection and after approximately two hours for each $B_1$, 0.5 µT (FIG. 20E), 0.7 µT (FIG. 20F), and 1.0 µT (FIG. 20G).

Figures 21A, 21B, 21C, 21D:
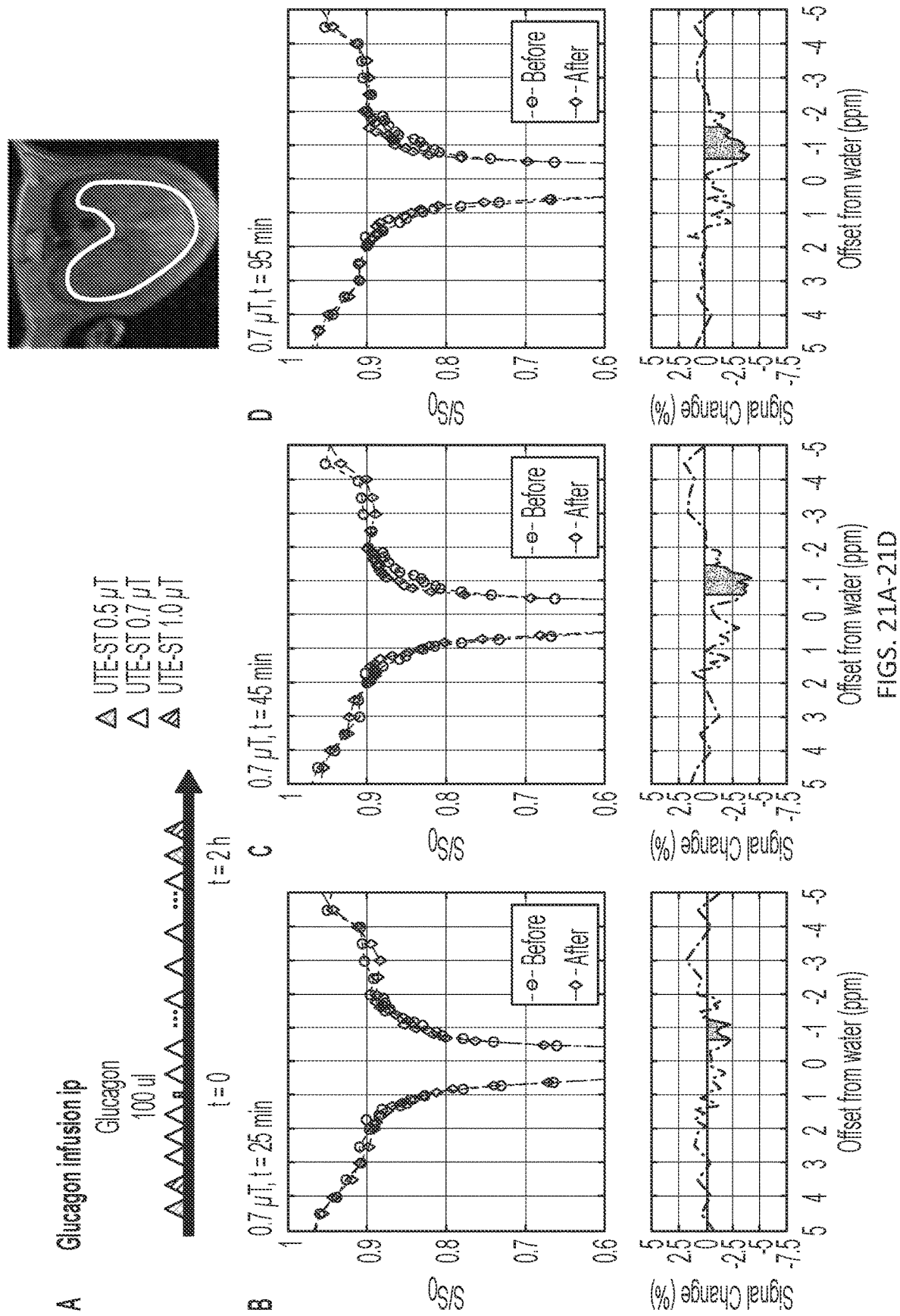
FIGS. 21A-21G show the effect of glucagon on mouse liver Z-spectra in a tenth mouse subject at 11.7 T.
Figures 21E, 21F, 21G:
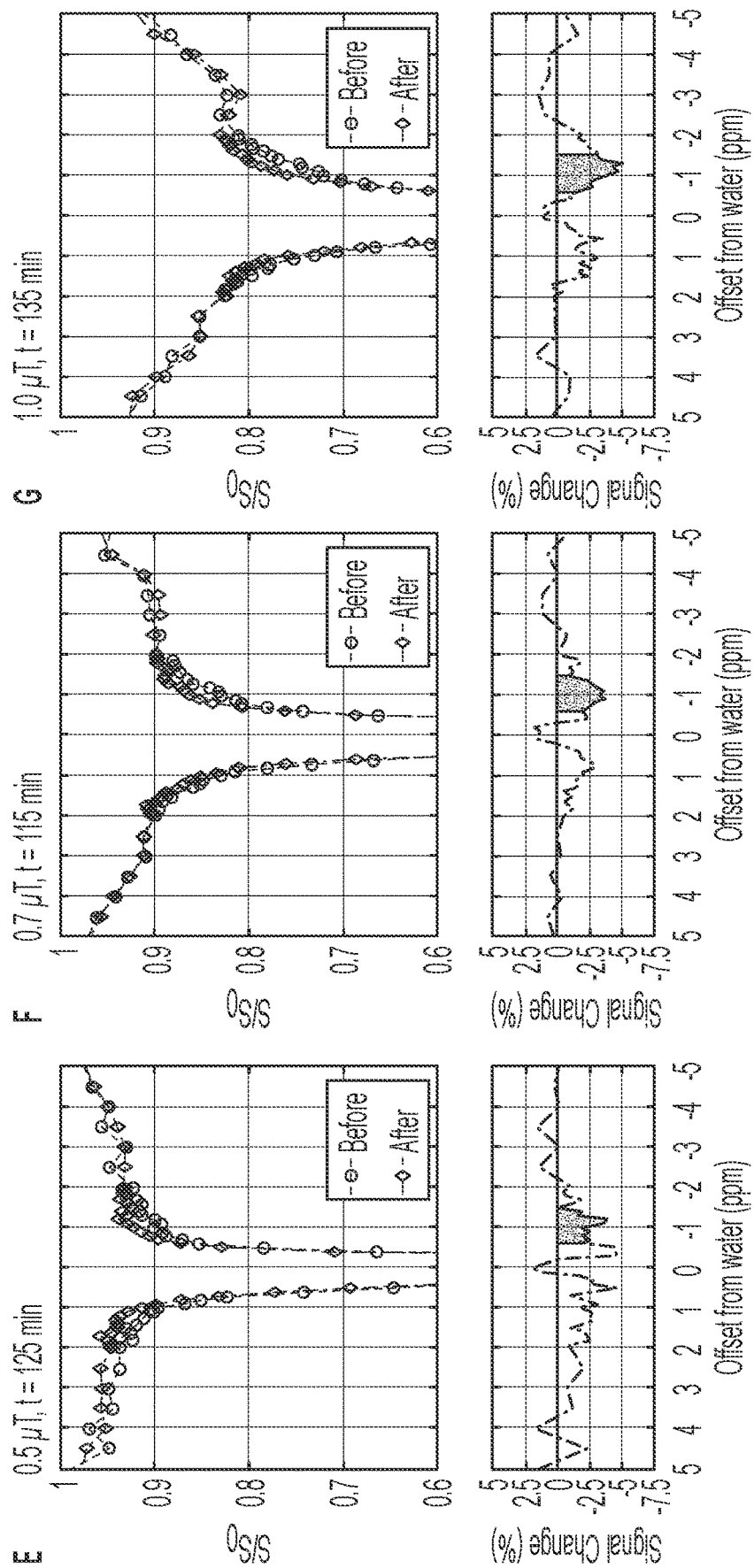

FIGS. 21A-21G show the effect of glucagon on mouse liver Z-spectra (mouse subject ten). FIG. 21A shows the UTE-ST pulse sequence at $B_1$ strengths of 0.5 µT, 0.7 µT, and 1.0 µT. In FIGS. 21B-21D, the time dependence after injection at $B_1$=0.7 µT is shown, at 25 minutes (FIG. 21B), 45 minutes (FIG. 21C), and 95 minutes (FIG. 21D). In FIGS. 21E to 21G, the $B_1$ dependence for signal difference is shown before injection and after approximately two hours for each $B_1$, 0.5 µT (FIG. 21E), 0.7 µT (FIG. 21F), and 1.0 µT (FIG. 21G).

Figure 22:
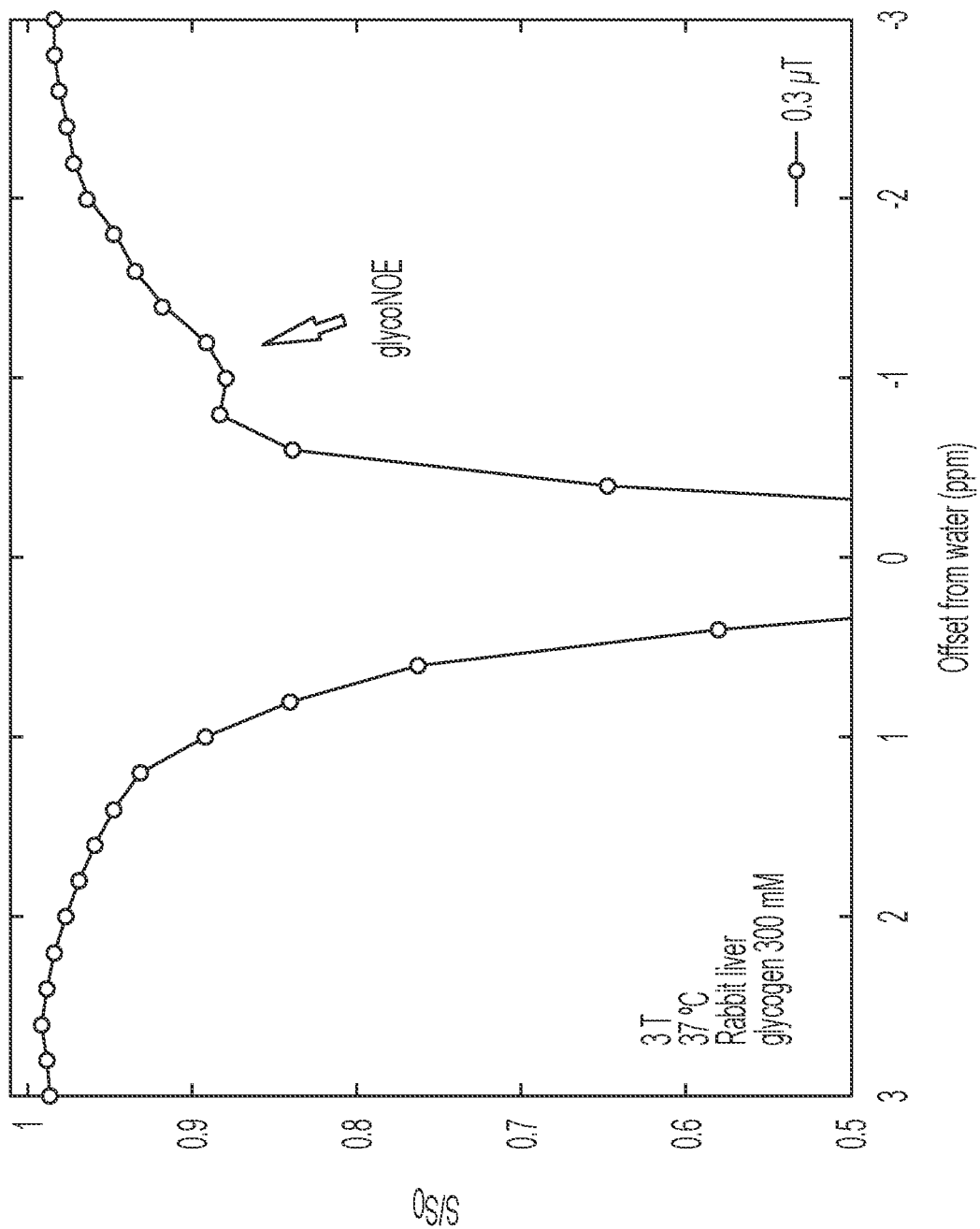
FIG. 22 shows glycoNOE in a rabbit liver phantom at a clinical MRI field strength (3T).

FIG. 22 shows glycoNOE at a clinical MRI field strength (3T). The Z-spectrum for rabbit liver glycogen (300 mM, pH 7.4, 37° C.) was acquired using a 3.0 T Philips Elition scanner (Philips, Best, Netherlands). The saturation consisted of a train of 80×50 ms gaussian-shaped RF pulses with zero inter-pulse delay. The saturation period (average $B_1$ 0.3 µT) was followed by a Turbo spin echo (TSE) image readout with TR/TE=10000/5 ms. Notice that to study glycoNOE effects at 3 T, the optimal saturation power needs to be lower compared to 11.7 T due to the smaller frequency difference between the glycoNOE peak and water peak (~130 Hz instead of ~507 Hz). While the width of the direct saturation in Hz is about comparable at both fields, it is thus about four times narrower in ppm at 11.7 T. Use of the same $B_1$ saturation pulse strength as at 11.7 T would therefore have much stronger direct saturation at the NOE frequency and this competing effect will reduce the measurable glycoNOE signal.

Experimental Discussion

The Z-spectra (FIGS. 2C and 8) of glycogen in vitro show resonances around both +0.6 ppm and −1 ppm. The results are consistent with previous MRS measurements on the glycogen NOE with water (27). Chen and coworkers (27) showed that saturation of water resulted in a reduction of H1-4 (+0.6 ppm) signal, and that the inversion of H1-4 resulted in NOEs for H3 (−0.7 ppm), H5 (−0.9 ppm) and H2+H4-1 (−1.1 ppm), demonstrating the NOE network of glycogen protons (H1-4, H3, H5, H2+H4-1) with water. However, in the Z-spectrum, the extent of the H1-4 NOE is small compared with the composite glycoNOE peak around −1 ppm (see pH 2.0 in FIG. 8) and it overlaps with the broad CEST signal from exchangeable OH protons. Therefore, the analysis focused on the composite −1 ppm glycoNOE signal, where four aliphatic protons (H3, H5, H2+H4-1) contribute with a signal enhanced by about two orders of magnitude relative to proton MRS. This relatively large signal enhancement using glycoNOE MRI allowed fast acquisition (currently 9 seconds per frequency point) at acceptable resolution (~0.3 mm) for in vivo imaging.

The results in vivo show that the distribution of the glycoNOE signal in the liver is heterogeneous. This agrees with previous observations that the liver glycogen content is highly dynamic and can vary dramatically depending on several factors such as health, the time after feeding and the distances to portal tracts and central veins (32). Considering that glycoNOE depends linearly on glycogen concentration (FIG. 2D and FIG. 16), the glycoNOE distribution should reflect local differences of glycogen levels. However, care has to be taken with such an interpretation, because particle size may in principle also contribute to the observed heterogeneity (FIG. 2B and FIG. 6). Note that different forms of glycogen coexist in liver, namely β particles (~$10^6$-$10^7$ Da) that have various diameters between 10 nm and 30 nm, and much larger α particles (up to over $10^9$ Da) that have diameters as high as 300 nm and likely have stronger NOE effects due to slower motion.

After fasting the mice for 24 hours, glycoNOE signal (N=5) decreases from 49±8%*ppm (equivalent to a glycogen concentration of about 47 mg/g wet liver, FIG. 16) to 6±8%*ppm (~6 mg/g). This is in agreement with a previous report that hepatic glycogen in mice is only 7% of its original concentration after 24 hours of fasting (33). The fasting data strongly support our assignment that the −1 ppm NOE signal in liver Z-spectra is mainly from glycogen. This was further confirmed by the glucagon injection experiments showing a strong reduction in the glycoNOE signal upon glucagon injection. These results are in agreement with the previous study of glycoCEST on perfused mouse liver, which showed signal reduction at both −1.0 ppm and +1.0 ppm under glucagon infusion (21). The reduction in glycoNOE (FIG. 4F) is interpreted to be a result of glycogen breaking down into glucose due to the effect of glucagon, while the decrease in signal at +0.5 ppm to +1.4 ppm cannot be interpreted as a direct consequence of this conversion process. The reason is that the liver glucosyl pool (the number of total glucosyl units in glucose and glycogen) is constant in the conversion reactions. Therefore, unless the glucose is removed by perfusion, the signal at around +1 ppm should not be reduced in this conversion and may even increase due to a higher number of OH groups in the +0.6 ppm to +3 ppm range. The reasons for the observed signal reduction at +0.5 ppm to +1.4 ppm could be a result of both glycogen H1-4 NOE signal loss and active export of glucose from the liver.

The decrease in glycoNOE signal in liver under the effects of fasting or glucagon due to metabolism may in principle be affected by a change in glycogen particle size. Glycogen average particle size has been suggested to fluctuate in the small range of about 15 to 30 nm (34) in mouse liver during this process. Similarly, possible spatial variations of glycogen particle size in liver may affect the glycoNOE signal distribution. Interestingly, however, a linear correspondence was found between chemical concentration measurement and the glycoNOE signal during fasting (FIG. 16), which suggests that particle size change is not a major issue (a notable role would cause a non-linear correlation). As a consequence, this measurement is used in FIG. 16 as a calibration and converted the glycoNOE into glycogen concentration.

Respiratory motion, blood flow, and arbitrary body movements may also increase the uncertainty in the glycoNOE signal. Although the glycoNOE maps can be generated with any type of MRI readout, an ultra-short echo time saturation transfer (UTE-ST) pulse sequence with a radial sampling scheme (35) was used to suppress respiratory motion artifacts in vivo. The observation that the glycoNOE signal for fasted liver is homogenously low (FIG. 3B) suggests artifacts from motion and small vessels are minimal. The consistency of the glycoNOE maps is further supported by measurements as a function of $B_1$ (FIGS. 9B-9D).

The current study demonstrates a novel way of directly imaging glycogen non-invasively in vivo or in vitro with enhanced sensitivity. It is based in some embodiments on the nuclear Overhauser enhancements between glycogen aliphatic protons and water protons, in contrast to the glycoCEST method which is based on the chemical exchange between glycogen hydroxyl protons and water protons. This glycoNOE approach is advantageous over glycoCEST for several reasons. First of all, the glycoNOE signal intensity was found to be minimally sensitive to pH and temperature (FIG. 2E), while glycoCEST experiments are affected by both pH and concentration changes rendering data interpretation less straightforward. While this temperature insensitivity may seem counterintuitive at first due to the sensitivity of NOEs to molecular motion, this can be understood by the glycoNOE effect being proportional to the ratio of two relaxation rates (see supplemental discussion). Secondly, glycoNOE MRI can be readily translated to human scanners (see data at 3T, FIG. 22), because the NOE transfer is slow, allowing efficient saturation and high signal visibility to be achieved with reasonably low $B_1$ strengths (on the order of 1 μT or less). Thirdly, the glycoNOE signal is easier to extract, while the glycoCEST signal is coalesced with the water peak. In addition, glycoCEST effects are often estimated based on an asymmetry analysis that quantifies glycoCEST as the saturation signal difference between "−1 ppm" and "+1 ppm" (21). The current study suggests that in some embodiments, such asymmetry analysis should not be used to assess glycogen changes as the glycoNOE and glycoCEST signals compensate each other in a proportion that will vary with concentration and the applied saturation strength, thus complicating absolute quantification. Last but not least, glycoNOE has better signal specificity for glycogen. For example, glycoNOE MRI can differentiate glycogen from glucose, while glycoCEST MRI cannot. The glycoCEST method is based on the exchange between the hydroxyl protons of glycogen and water, but many other molecules in vivo, especially glucose and its analogs, have hydroxyl protons resonating at ~+1 ppm as well. The glycoCEST in reality measures the total contribution of any molecules that contain hydroxyl groups resonating at ~+1 ppm. In contrast, the signal at glycoNOE position (−1 ppm) in the liver could be mostly removed in some embodiments by fasting or glucagon injection, showing that its contamination by other metabolites is limited. When studying muscle, the interpretation of glycoCEST becomes even more difficult because signals from abundant metabolites such as creatine (guanidinium protons at +2 ppm) and phosphocreatine (36) may contaminate the glycoCEST effect at lower field strengths, where the exchange regime is faster than at 11.7 T. This field dependence of the proton exchange regime minimally affects the glycoNOE signals (FIG. 22).

It is important to note that almost 100% of glycogen is visible in both in vivo and in vitro $^{13}$C MRS (16) and also in $^1$H MRS of glycogen in $D_2O$ (17), while glycogen in vivo is greatly underestimated by $^1$H MRS (20). This underestimation of glycogen by $^1$H MRS could not be explained by the existence of a significant "hidden" population of glycogen with extremely short T2 relaxation time, as $^{13}$C MRS (16, 37) results showed the opposite. The current study suggests that in some embodiments, the underestimation of glycogen in vivo by $^1$H MRS likely results from the water suppression techniques used in these experiments (20). The pre-saturation of the water peak can reduce the glycogen proton signal by as high as ~55% (27) due to the saturation transfer discussed above, causing glycogen to be underestimated by $^1$H MRS with water suppression in $H_2O$ but not in $D_2O$.

Conclusion

The specific mapping of hepatic glycogen with enhanced sensitivity was demonstrated using glycoNOE MRI. The hypothesis that glycogen protons have a −1 ppm composite NOE signal in Z-spectra was validated both in vitro, and in mouse liver in vivo, using fasting and glucagon injection experiments on mice. As glycogen is present in the heart, liver, skeletal muscle, brain, and even tumor tissues, the proposed glycoNOE MRI method has the potential in some embodiments to be applied to assess function and diseases in these and other tissues.

The above provides examples according to particular embodiments of the current invention. The broad concepts of the current invention are not limited to only those particular examples.

The following appendices describe additional embodiments of the current invention in more detail; however, the general concepts of the current invention are not to be limited to these particular examples.

Materials and Methods

Ultra-Short Echo Time Saturation Transfer (UTE-ST) MRI

MRI experiments were performed on an 11.7 T (500 MHz) Bruker Biospec preclinical scanner (Bruker, Ettlingen, Germany) equipped with a 72 mm quadrature volume resonator for transmission and an 8-channel phased array RF coil for reception, unless specified otherwise. An ultra-short echo time (UTE) saturation transfer MRI pulse sequence with a radial acquisition scheme, described in detail elsewhere (35), was used to acquire all data. In each repetition time (TR) of UTE-ST, a 20 ms Gaussian-shaped saturation pulse was used to label the proton pool at a certain frequency followed by the UTE readout. The inter-pulse delay mixing time was 10 ms, the excitation pulse for the UTE readout was a 0.3 ms Gaussian pulse. The effective echo time (TE) was 0.38 ms, total TR was 30 ms. The number of radial spokes was 302 for each frequency. The scan time for one saturation frequency image was 9 seconds (302*30 ms).

In Vitro Experiments on Glycogen

Rabbit liver glycogen (Type III G8876, CAS no. 9005-79-2) and bovine liver glycogen (Type 1X G0885, CAS no. 9005-79-2) from Sigma (St. Louis, MO) were dissolved in phosphate-buffered saline (PBS, 152 mM Na/9.6 mM Pi). (a) For both rabbit liver glycogen and bovine liver glycogen, solutions with glucose unit concentrations of 25, 50, 100, 150, 200 and 300 mM and the same pH of 7.4 were prepared. (b) To examine pH effects, rabbit liver glycogen solutions with pH of 2.0, 3.0, 4.0, 5.5, 6.0, 6.5, 7.0, 7.4, 8.0 and 9.0, and the same glucose unit concentration of 100 mM were made. Experiments were carried out at 20° C. or 37° C. (c) To examine temperature effects on the measurements, scans on a rabbit liver sample set (b) were first conducted at 20° C. and subsequently at 37° C. (1 hour of waiting for thermal equilibrium) using a 23 mm volume coil (for both transmit and receive) that was equipped with a heater and temperature sensor module.

Four different saturation $B_1$ strengths (0.5, 0.7, 1.0 and 1.5 μT) were used for UTE-ST scans on glycogen in vitro. The saturation frequency offsets were: 200, 200, 200, 8, 7, 6, 5 ppm, then every 0.1 ppm to 0 ppm, then 200, 200, 200, 200, −8, −7, −6, −5 ppm, then every 0.1 ppm to −0.1 ppm (a "converge sampling" scheme). The total time used for one Z-spectrum was 17 mins 22 secs.

In Vivo Liver glycoNOE MRI of Fed and Fasted Mice

All experiments were performed with the approval of and in accordance with Johns Hopkins University Animal Care and Use Committee guidelines. Five healthy fed adult mice were scanned with MRI before fasting and after 24-28 hours of fasting. Fed mice were studied at least 6 hours after starting food consumption. A 2 mm slice thickness with in-plane resolution of 0.3 mm was used and UTE-ST scans were acquired with the same parameters as the in vitro experiments.

In Vivo Liver glycoNOE MRI of Mouse Liver Before and After Intraperitoneal Infusion of Glucagon Prior to the start of glucagon infusion, three baseline Z-spectra ($B_1$=0.7 μT) were acquired. To reduce the hepatic glycogen, 100 μl of glucagon (porcine glucagon, CAS no. 16941-32-5; Purity: 95.13%, MedChemExpress, NJ, USA) solution with a concentration of 1.0 mg/ml was injected intraperitoneally within 10 seconds. Immediately after the injection, 12 repetitive UTE-ST scans with a $B_1$ strength of 0.7 μT were performed (10 mins per scan). Additional scans with $B_1$ of 0.5 μT and 1.0 μT were conducted before infusion and at 120 min and 130 min post-infusion. The saturation frequencies were: 200, 200, 200, 8, 7, 6, 5, 4.5, 4, 3.5, 3, 2.5, 2, 1.9, 1.8, . . . , 0.1, 0, 200, 200, 200, −8, −7, −6, −5, −4.5, . . . , −2.5, −2, 1.9, −1.8, . . . , −0.1 ppm ("converge sampling"). Mice were sacrificed after the experiments.

Chemical Assay of Liver Glycogen Content

After glycoNOE MRI, liver tissues were immediately isolated from the mice, "flash frozen" on dry ice and stored at −80° C. The protocol for extraction of liver glycogen has been fully described elsewhere (16, 38). Briefly, each 200 mg minced liver tissue was mixed with 800 μl 30% KOH solution, heated in boiling water for 30 mins, and centrifuged at 2000 g for 10 mins to remove insoluble components. The supernatant was mixed with 1.5 volume of 100% ethanal to precipitate glycogen, and centrifuged at 4000 g for 20 mins. The glycogen pellet was lyophilized, and measured using a fluorometric Glycogen Assay Kit (Cayman Chemical #700480). As water in liver is about 71% of liver weight (39), 1 mg glycogen per g wet liver is equivalent to ~8.4 mM glucosyl units (168 g/mol) in solution.

Data Analysis

Static field ($B_0$) inhomogeneities were corrected in each scan on a voxel-by-voxel basis by fitting for the drift of the direct water saturation chemical shift in each Z-spectrum (40). For each in vitro glycogen Z-spectrum, the negative half (−0.2 ppm to −5 ppm) was assumed to consist of two resonances, one centered at 0 ppm (water peak) and another around −1.0 ppm (glycoNOE). These were fitted with Lorentzian shapes (31) on a voxel-by-voxel basis. The water line in the positive range of Z-spectrum was assumed to be the mirror of that in the negative half. The fitted glycoNOE peak height was used as the estimated glycoNOE signal intensity. For each in vivo Z-spectrum, the negative range was assumed to consist of a constant magnetization transfer contrast (MTC) background plus four resonances, each centered at 0 ppm (water peak), −1.0 ppm (glycoNOE), around −3.0 ppm (broad NOE component) and −3.9 ppm. This range was fitted using a multi-Lorentzian shape analysis. The glycoNOE map was constructed based on the integral of the estimated 1 ppm glycoNOE peak (10 points from −0.6 ppm to −1.5 ppm) for each voxel.

To calculate the glycoNOE change after glucagon injection, the scan right before the glucagon injection was used as reference. Z-spectra from each voxel were frequency corrected. To account for spectral baseline drift after the infusion of glucagon, the spectral intensities between −8 ppm to −2 ppm and +2 ppm to +8 ppm were used as a reference for spectral intensity alignment. Aligned Z-spectra were subtracted from the reference Z-spectra to obtain the differences spectra. The integral of the region from −0.6 ppm to −1.5 ppm in the Z-spectral differences was used as the measure of glycoNOE changes.

Glycogen plays a central role in glucose homeostasis and is abundant in several types of tissue. Some embodiments report a novel MRI method for imaging glycogen non-invasively with enhanced detection sensitivity and high specificity, using the magnetic coupling between glycogen and water protons through the nuclear Overhauser enhancement (NOE). Some embodiments show in vitro that the glycogen NOE (glycoNOE) signal is correlated linearly with glycogen concentration, while pH and temperature have little effect on its intensity. For validation, glycoNOE signal changes were imaged in mouse liver, both before and after fasting and during glucagon infusion. The glycoNOE signal was reduced by 88±16% (N=5) after 24 hours of fasting and by 76±22% (N=5) at one hour after intraperitoneal injection of glucagon, which is known to rapidly deplete hepatic glycogen. The ability to non-invasively image glycogen should allow assessment in some embodiments of diseases in which glucose metabolism or storage is altered, for example, diabetes, cardiac disease, muscular disorders, cancer, and glycogen storage diseases.

Supplemental Discussion

The Influence of Temperature on the glycoNOE Signal a) Z-Spectral Changes.

Changes in temperature slightly shift the frequency of the glycoNOE peak (e.g. FIG. 8) due to the dependence of the water frequency on temperature (42), while aliphatic protons generally have no temperature dependence. This is a disadvantage of referencing to the water signal in Z-spectra, but this is the common approach. In addition to this shift, the shape of the water signal will change with temperature due to the coalescence of the OH proton signal with that of the water signal, as the exchange rates are in the intermediate to fast exchange regime. This effect depends on temperature since temperature affects the OH exchange rate. However, this all occurs in the broad baseline and does not affect the determination of the glycoNOE effect, as can be seen in FIG. 8. This is similar to pH effects, which affect the glycoCEST and Z-spectral shape, but not the glycoNOE effect in buffered water solutions, as discussed in the appendix below (FIG. 8 and FIG. 2).

b) Changes in glycoNOE Effect Size.

The experimental data (FIG. 2E) show that glycoNOE signal intensity is relatively unaffected by temperature changes. While counterintuitive at first, this temperature-insensitivity can be explained in terms of the temperature-dependent molecular motion of both water and glycogen. The water NOE signal strength is a function of both the $T_1$ relaxation of water ($T_{1w}$) and NOE cross-relaxation rate ($\sigma$) (43), $$glycoNOE \propto \sigma * T_{1w} \qquad [S1]$$

where NOE dipolar cross-relaxation rate $\sigma$ is a function of molecular motion (glycogen proton rotational correlation time, $\tau_c$) (44).

$$\sigma = \frac{1}{4}\left(\frac{\mu_0}{4\pi}\right)^2 \left(\frac{h\gamma_H^2}{r^3}\right)^2 [-\tau_c + 6\frac{\tau_c}{1+(2\omega\tau_c)^2}]. \qquad [S2]$$

Here, $\mu_0$ is the permeability of vacuum; r is the interproton distance; $\gamma_H$ is the gyromagnetic ratio of proton; h is Planck's constant divided by $2\pi$. $\omega$ is the angular Larmor frequencies. The correlation time $\tau_c$ in glycogen has been reported to be around 5 ns, (45, 46) but this value varies depending on the glycogen size and temperature. From Eq. 2, accounting for $\omega\tau_c \gg 1$ at high magnetic field, $$\sigma \propto \tau_c. \qquad [S3]$$

The water relaxation rate ($1/T_{1w}$) similarly is a function of water molecular motion (water proton correlation time, $\tau_w$) in the glycogen coordination sphere where the transfer takes place (47):

$$\frac{1}{T_{1w}} \propto \tau_w. \qquad [S4]$$

Therefore, from Eqs. S1-S4, $$glycoNOE \propto \sigma * T_{1w} \propto \frac{\tau_c}{\tau_w}. \qquad [S5]$$

Both $\tau_c$ and $\tau_w$ are dependent on temperature (T) (47-49), $$\tau \propto e^{E\alpha/RT} \qquad [S6]$$

where R is the gas constant, $E_\alpha$ is the apparent activation energy for the motion. Therefore, a temperature change will induce opposite changes in $\sigma$ and $T_{1w}$ (48, 49). The experimental glycoNOE quantification data (FIG. 2E) indicate a negligible temperature effect over the current experimental range, which is tentatively attributed to this compensatory effect.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® NT/98/2000/XP/Vista/Windows 7/8/etc. available from MICROSOFT® Corporation of Redmond, Wash., U.S.A. or an Apple computer executing MAC® OS from Apple® of Cupertino, Calif, U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but is not limited to) a hard disk drive and/or a removable storage drive, representing a floppy diskette drive, a magnetic tape drive, an optical disk drive, a compact disk drive CD-ROM, flash memory, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

The computer may also include an input device may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or other camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

REFERENCES

1. R. B. van Heeswijk, F. D. Morgenthaler, L. Xin, R. Gruetter, Quantification of brain glycogen concentration and turnover through localized $^{13}C$ NMR of both the C1 and C6 resonances. *NMR in Biomedicine* 23, 270-276 (2010).
2. A. M. Brown, B. R. Ransom, Astrocyte glycogen and brain energy metabolism. *Glia* 55, 1263-1271 (2007).

3. R. Gruetter et al., Validation of $^{13}$C NMR measurements of liver glycogen in vivo. *Magnetic resonance in medicine* 31, 583-588 (1994).
4. M. Konig, S. Bulik, H.-G. Holzhütter, Quantifying the contribution of the liver to glucose homeostasis: a detailed kinetic model of human hepatic glucose metabolism. *PLoS computational biology* 8, e1002577 (2012).
5. S. L. Henning, R. B. Wambolt, B. O. Schönekess, G. D. Lopaschuk, M. F. Allard, Contribution of glycogen to aerobic myocardial glucose utilization. *Circulation* 93, 1549-1555 (1996).
6. T. Price, D. Rothman, M. Avison, P. Buonamico, R. Shulman, $^{13}$C-NMR measurements of muscle glycogen during low-intensity exercise. *Journal of Applied Physiology* 70, 1836-1844 (1991).
7. N. Ørtenblad, H. Westerblad, J. Nielsen, Muscle glycogen stores and fatigue. *The Journal of physiology* 591, 4405-4413 (2013).
8. M. Rousset, A. Zweibaum, J. Fogh, Presence of glycogen and growth-related variations in 58 cultured human tumor cell lines of various tissue origins. *Cancer research* 41, 1165-1170 (1981).
9. E. Favaro et al., Glucose utilization via glycogen phosphorylase sustains proliferation and prevents premature senescence in cancer cells. *Cell metabolism* 16, 751-764 (2012).
10. I. Magnusson, D. Rothman, L. Katz, R. Shulman, G. Shulman, Increased rate of gluconeogenesis in type II diabetes mellitus. A $^{13}$C nuclear magnetic resonance study. *The Journal of clinical investigation* 90, 1323-1327 (1992).
11. M. Krssak et al., Alterations in postprandial hepatic glycogen metabolism in type 2 diabetes. *Diabetes* 53, 3048-3056 (2004).
12. M. M. Adeva-Andany, M. González-Lucán, C. Donapetry-García, C. Fernández-Fernández, E. Ameneiros-Rodriguez, Glycogen metabolism in humans. *BBA clinical* 5, 85-100 (2016).
13. L. Krähenbühl et al., Reduced hepatic glycogen stores in patients with liver cirrhosis. *Liver international* 23, 101-109 (2003).
14. D. C. Nieman, R. A. Shanely, K. A. Zwetsloot, M. P. Meaney, G. E. Farris, Ultrasonic assessment of exercise-induced change in skeletal muscle glycogen content. *BMC sports science, medicine and rehabilitation* 7, 9 (2015).
15. T. H. Witney et al., A novel radiotracer to image glycogen metabolism in tumors by positron emission tomography. *Cancer research* 74, 1319-1328 (2014).
16. L. O. Sillerud, R. G. Shulman, Structure and metabolism of mammalian liver glycogen monitored by carbon-13 nuclear magnetic resonance. *Biochemistry* 22, 1087-1094 (1983).
17. L.-H. Zang, D. L. Rothman, R. G. Shulman, $^1$H NMR visibility of mammalian glycogen in solution. *Proceedings of the National Academy of Sciences* 87, 1678-1680 (1990).
18. K. Heinicke et al., Reproducibility and absolute quantification of muscle glycogen in patients with glycogen storage disease by $^{13}$C NMR spectroscopy at 7 Tesla. *PloS one* 9, e108706 (2014).
19. W. Roser, N. Beckmann, U. Wiesmann, J. Seelig, Absolute quantification of the hepatic glycogen content in a patient with glycogen storage disease by $^{13}$C magnetic resonance spectroscopy. *Magnetic resonance imaging* 14, 1217-1220 (1996).
20. R. Ouwerkerk, R. I. Pettigrew, A. M. Gharib, Liver metabolite concentrations measured with $^1$H MR spectroscopy. *Radiology* 265, 565-575 (2012).
21. P. C. Van Zijl, C. K. Jones, J. Ren, C. R. Malloy, A. D. Sherry, MRI detection of glycogen in vivo by using chemical exchange saturation transfer imaging (glycoCEST). *Proceedings of the National Academy of Sciences* 104, 4359-4364 (2007).
22. C. O. Miller et al., Noninvasive measurements of glycogen in perfused mouse livers using chemical exchange saturation transfer NMR and comparison to $^{13}$C NMR spectroscopy. *Analytical chemistry* 87, 5824-5830 (2015).
23. G. L. Simegn, A. J. Van der Kouwe, F. C. Robertson, E. M. Meintjes, A. Alhamud, Real-time simultaneous shim and motion measurement and correction in glycoCEST MRI using double volumetric navigators (DvNavs). *Magnetic resonance in medicine* 81, 2600-2613 (2019).
24. P. C. Van Zijl, N. N. Yadav, Chemical exchange saturation transfer (CEST): what is in a name and what isn't? *Magnetic resonance in medicine* 65, 927-948 (2011).
25. K. Sagiyama, S. Zhang, I. Dimitrov, A. Sherry, M. Takahashi (2014) In vivo monitoring of liver glycogen by chemical exchange saturation transfer imaging (Glyco-CEST) in live mice. in *Proceedings of the International Society for Magnetic Resonance in Medicine, p 0762*.
26. M. Deng et al., Chemical exchange saturation transfer (CEST) MR technique for liver imaging at 3.0 Tesla: an evaluation of different offset number and an after-meal and over-night-fast comparison. *Molecular Imaging and Biology* 18, 274-282 (2016).
27. W. Chen, M. J. Avison, X. H. Zhu, R. G. Shulman, NMR studies of proton NOEs in glycogen. *Biochemistry* 32, 11483-11487 (1993).
28. W. Ling, R. R. Regatte, G. Navon, A. Jerschow, Assessment of glycosaminoglycan concentration in vivo by chemical exchange-dependent saturation transfer (gagCEST). *Proceedings of the National Academy of Sciences* 105, 2266-2270 (2008).
29. N. N. Yadav et al., Detection of dynamic substrate binding using MRI. *Scientific reports* 7, 10138 (2017).
30. L.-H. Zang, A. M. Howseman, R. G. Shulman, Assignment of the $^1$H chemical shifts of glycogen. *Carbohydrate research* 220, 1-9 (1991).
31. K. L. Desmond, F. Moosvi, G. J. Stanisz, Mapping of amide, amine, and aliphatic peaks in the CEST spectra of murine xenografts at 7 T. *Magnetic resonance in medicine* 71, 1841-1853 (2014).
32. B. Giffin, R. Drake, R. Morris, R. Cardell, Hepatic lobular patterns of phosphoenolpyruvate carboxykinase, glycogen synthase, and glycogen phosphorylase in fasted and fed rats. *Journal of Histochemistry & Cytochemistry* 41, 1849-1862 (1993).
33. T. Jensen, M. Kiersgaard, D. B. Sorensen, L. Mikkelsen, Fasting of mice: a review. *Laboratory Animals* 47, 225-240 (2013).
34. M. A. Sullivan et al., Changes in glycogen structure over feeding cycle sheds new light on blood-glucose control. *Biomacromolecules* 15, 660-665 (2014).
35. L. Chen et al., Protein aggregation linked to Alzheimer's disease revealed by saturation transfer MRI. *NeuroImage* 188, 380-390 (2019).
36. L. Chen, P. B. Barker, R. G. Weiss, P. C. van Zijl, J. Xu, Creatine and phosphocreatine mapping of mouse skeletal muscle by a polynomial and Lorentzian line-shape fitting CEST method. *Magnetic resonance in medicine* 81, 69-78 (2019).

37. L. H. Zang, M. R. Laughlin, D. L. Rothman, R. G. Shulman, Carbon-13 NMR relaxation times of hepatic glycogen in vitro and in vivo. *Biochemistry* 29, 6815-6820 (1990).
38. H. Shokri-Afra, A. Ostovar-Ravari, M. Rasouli, Improvement of the classical assay method for liver glycogen fractions: ASG is the main and metabolic active fraction. *European Review for Medical and Pharmacological Sciences* 20, 4328-4336 (2016).
39. O. Strubelt et al., The influence of fasting on the susceptibility of mice to hepatotoxic injury. *Toxicology and applied pharmacology* 60, 66-77 (1981).
40. M. Kim, J. Gillen, B. A. Landman, J. Zhou, P. C. Van Zijl, Water saturation shift referencing (WASSR) for chemical exchange saturation transfer (CEST) experiments. *Magnetic Resonance in Medicine* 61, 1441-1450 (2009).
41. Y. Zhou et al., Data from "Magnetic resonance imaging of glycogen using its magnetic coupling with water." Open Science Framework. https.//osf.io/xmbst/. Deposited 13 Oct. 2019.
42. Y. Ishihara et al., A precise and fast temperature mapping using water proton chemical shift. *Magnetic resonance in medicine* 34, 814-823 (1995).
43. W. Ling, R. R. Regatte, G. Navon, A. Jerschow, Assessment of glycosaminoglycan concentration in vivo by chemical exchange-dependent saturation transfer (gagCEST). *Proceedings of the National Academy of Sciences* 105, 2266-2270 (2008).
44. P. Allard, M. Helgstrand, T. Härd, The complete homogeneous master equation for a heteronuclear two-spin system in the basis of Cartesian product operators. *Journal of Magnetic Resonance* 134, 7-16 (1998).
45. W. Chen, M. J. Avison, X. H. Zhu, R. G. Shulman, NMR studies of proton NOEs in glycogen. *Biochemistry* 32, 11483-11487 (1993).
46. L. H. Zang, M. R. Laughlin, D. L. Rothman, R. G. Shulman, Carbon-13 NMR relaxation times of hepatic glycogen in vitro and in vivo. *Biochemistry* 29, 6815-6820 (1990).
47. N. Bloembergen, E. M. Purcell, R. V. Pound, Relaxation effects in nuclear magnetic resonance absorption. *Physical review* 73, 679 (1948).
48. M. Tylianakis, A. Spyros, P. Dais, F. R. Taravel, A. Perico, NMR study of the rotational dynamics of linear homopolysaccharides in dilute solutions as a function of linkage position and stereochemistry. *Carbohydrate research* 315, 16-34 (1999).
49. J. Simpson, H. Carr, Diffusion and nuclear spin relaxation in water. *Physical Review* 111, 1201 (1958).

We claim:

1. A system for magnetic resonance imaging of polysaccharide molecules, comprising:
    a primary magnet configured to provide a magnetic field that is sufficiently homogeneous over an imaging volume;
    a magnetic gradient coil configured to generate a spatial encoding in the magnetic field;
    a radiofrequency coil configured to acquire one or more water proton signal intensity measurements at each of a plurality of voxels within the imaging volume, wherein said signal intensity measurements are acquired in each voxel at a one or more irradiation frequencies, said irradiation frequencies at lower parts-per-million (ppm) than a baseline frequency associated with free water protons; and
    a data processor configured to:
        generate, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume; and
        generate, using a calibration of the water proton signal intensity measurements for said rNOE exchange process, a concentration map of the polysaccharide molecules in the imaging volume.

2. A method for magnetic resonance imaging of polysaccharide molecules, comprising:
    providing a magnetic field that is sufficiently homogeneous over an imaging volume;
    generating a spatial encoding in the magnetic field;
    acquiring one or more water proton signal intensity measurements at each of a plurality of voxels within the imaging volume, wherein said signal intensity measurements are acquired in each voxel at a one or more irradiation frequencies, said irradiation frequencies at lower parts-per-million (ppm) than a baseline frequency associated with free water protons;
    generating, based on the water proton signal intensity measurements in each voxel, a water proton signal intensity map of the relayed Nuclear Overhauser Effect (rNOE) exchange process of aliphatic protons in the polysaccharide molecules to free water protons in the imaging volume; and
    generating, using a calibration of the water proton signal intensity measurements for said rNOE exchange process, a concentration map of the polysaccharide molecules in the imaging volume.

3. The system of claim 1, wherein the water proton signal intensity measurements are acquired after irradiation of the imaging volume using a magnetic labelling pulse sequence.

4. The system of claim 1, wherein the data processor is further configured to generate the water proton signal intensity map based on a plurality of resonances associated with magnetization transfer of aliphatic protons to free water via the rNOE process.

5. The system of claim 1, wherein the polysaccharide molecules comprise one of glycogen molecules, chemically modified polysaccharide molecules, labelled polysaccharide molecules, polysaccharides connected to binding substrates, endogenous polysaccharides, and exogenous polysaccharides.

6. The system of claim 1, wherein the imaging volume comprises at least one of a tumor, a brain, a heart, a liver, and a skeletal muscle.

7. The system of claim 1,
    wherein the one or more water proton signal intensity measurements are a plurality of signal intensity measurements comprising one or more water proton signal intensity measurements acquired in each voxel at a one or more additional irradiation frequencies, said additional irradiation frequencies at lower ppm than the baseline frequency associated with free water protons,
    wherein the data processor is further configured to correct the plurality of water proton signal intensity measurements based on a mixed direct water saturation and magnetization transfer contrast (MTC) background.

8. The system of claim 1, wherein the concentration map of the polysaccharide molecules is sensitive to the size of polysaccharide molecules within each voxel.

9. The system of claim 1, wherein the concentration map of the polysaccharide molecules is sensitive to the concentration of polysaccharide molecules within each voxel.

10. The system of claim 1, wherein the concentration map of the polysaccharide molecules is statistically independent of temperature.

11. The system of claim 1, wherein the concentration map of the polysaccharide molecules is statistically independent of pH.

12. The system of claim 1,
wherein the water proton signal intensity measurements are acquired prior to an administration of exogenous polysaccharides to the imaging volume,
wherein the radiofrequency coil is further configured to acquire one or more water proton signal intensity measurements at each of the plurality of voxels within the imaging volume, subsequent to the administration of exogenous polysaccharides, and
wherein the data processor is further configured to generate a series of concentration maps of the polysaccharide molecules in the imaging volume, said series of concentration maps characterizing a temporal variation of the concentration of polysaccharides in the imaging volume due to the administration of exogenous polysaccharides.

13. The system of claim 1,
wherein the water proton signal intensity measurements are acquired prior to an intervention that modifies endogenous polysaccharides in the imaging volume,
wherein the radiofrequency coil is further configured to acquire one or more water proton signal intensity measurements at each of the plurality of voxels within the imaging volume, subsequent to the intervention, and
wherein the data processor is further configured to generate a series of concentration maps of the polysaccharide molecules in the imaging volume, said series of concentration maps characterizing a temporal variation of the concentration of polysaccharides in the imaging volume due to the intervention.

14. The method of claim 2, wherein the water proton signal intensity measurements are acquired after irradiation of the imaging volume using a magnetic labelling pulse sequence.

15. The method of claim 2, wherein generating the water proton signal intensity map is based on a plurality of resonances associated with magnetization transfer of aliphatic protons to free water via the rNOE process.

16. The method of claim 2, wherein the polysaccharide molecules comprise one of glycogen molecules, chemically modified polysaccharide molecules, labelled polysaccharide molecules, polysaccharides connected to binding substrates, endogenous polysaccharides, and exogenous polysaccharides.

17. The method of claim 2, wherein the imaging volume comprises at least one of a tumor, a brain, a heart, a liver, and a skeletal muscle.

18. The method of claim 2,
wherein the one or more water proton signal intensity measurements are a plurality of signal intensity measurements comprising one or more water proton signal intensity measurements acquired in each voxel at a one or more additional irradiation frequencies, said additional irradiation frequencies at lower ppm than the baseline frequency associated with free water protons, the method further comprising correcting the plurality of water proton signal intensity measurements based on a mixed direct water saturation and magnetization transfer contrast (MTC) background.

19. The method of claim 2, wherein the concentration map of the polysaccharide molecules is sensitive to the size of polysaccharide molecules within each voxel.

20. The method of claim 2, wherein the concentration map of the polysaccharide molecules is sensitive to the concentration of polysaccharide molecules within each voxel.

21. The method of claim 2, wherein the concentration map of the polysaccharide molecules is statistically independent of temperature.

22. The method of claim 2, wherein the concentration map of the polysaccharide molecules is statistically independent of pH.

23. The method of claim 2, wherein the water proton signal intensity measurements are acquired prior to an administration of exogenous polysaccharides to the imaging volume, the method further comprising:
acquiring one or more water proton signal intensity measurements at each of the plurality of voxels within the imaging volume, subsequent to the administration of exogenous polysaccharides; and
generating a series of concentration maps of the polysaccharide molecules in the imaging volume, said series of concentration maps characterizing a temporal variation of the concentration of polysaccharides in the imaging volume due to the administration of exogenous polysaccharides.

24. The method of claim 2, wherein the water proton signal intensity measurements are acquired prior to an intervention that modifies endogenous polysaccharides in the imaging volume, the method further comprising:
acquiring one or more water proton signal intensity measurements at each of the plurality of voxels within the imaging volume, subsequent to the intervention, and
generating a series of concentration maps of the polysaccharide molecules in the imaging volume, said series of concentration maps characterizing a temporal variation of the concentration of polysaccharides in the imaging volume due to the intervention.

25. The system of claim 3, wherein the magnetic labeling pulse sequence is one of a saturation transfer pulse sequence, an inversion pulse sequence, and an excitation pulse sequence.

26. The system of claim 12, wherein the administration of exogenous polysaccharides comprises an injection of a contrast agent which comprises polysaccharide molecules.

27. The system of claim 13, wherein the intervention comprises one of an administered drug or chemical compound, an exercise regimen, an intake of food, and a fasting regimen.

28. The method of claim 14, wherein the magnetic labeling pulse sequence is one of a saturation transfer pulse sequence, an inversion pulse sequence, and an excitation pulse sequence.

29. The method of claim 23, wherein the administration of exogenous polysaccharides comprises an injection of a contrast agent which comprises polysaccharide molecules.

30. The method of claim 24, wherein the intervention comprises one of an administered drug or chemical compound, an exercise regimen, an intake of food, and a fasting regimen.

* * * * *